(12) United States Patent
Nakayama et al.

(10) Patent No.: US 7,074,837 B2
(45) Date of Patent: Jul. 11, 2006

(54) PROCESSES FOR PREPARATION OF BICYCLIC COMPOUNDS AND INTERMEDIATES THEREFOR

(75) Inventors: Keiji Nakayama, Edogawa-ku (JP); Makoto Muto, Edogawa-ku (JP); Tatsuru Saito, Edogawa-ku (JP); Yuichiro Tani, Edogawa-ku (JP); Toshifumi Akiba, Edogawa-ku (JP)

(73) Assignee: Daiichi Pharmaceutical Co., Ltd., Tokyo (JP)

( * ) Notice: Subject to any disclaimer, the term of this patent is extended or adjusted under 35 U.S.C. 154(b) by 115 days.

(21) Appl. No.: 10/344,272

(22) PCT Filed: Aug. 7, 2001

(86) PCT No.: PCT/JP01/06786

§ 371 (c)(1),
(2), (4) Date: Feb. 10, 2003

(87) PCT Pub. No.: WO02/14278

PCT Pub. Date: Feb. 21, 2002

(65) Prior Publication Data

US 2004/0019223 A1    Jan. 29, 2004

(30) Foreign Application Priority Data

Feb. 21, 2001    (JP)    ............... 2001-044402

(51) Int. Cl.
*A61K 31/357*    (2006.01)
*A61K 31/11*    (2006.01)
*C07D 317/14*    (2006.01)
*C07D 319/06*    (2006.01)
*C07C 47/11*    (2006.01)

(52) U.S. Cl. ............ 514/693; 549/430; 568/445; 514/463

(58) Field of Classification Search ............... 568/445; 549/430; 514/693, 463
See application file for complete search history.

(56) References Cited

FOREIGN PATENT DOCUMENTS

| EP | 94633 | 11/1983 |
|---|---|---|
| EP | 357047 | 3/1990 |
| JP | 8-157455 | 6/1996 |
| JP | 11-49750 | 2/1999 |
| JP | 2002322114 | * 11/2002 |
| WO | WO-96/37470 | * 11/1996 |
| WO | WO 96/37470 | 11/1996 |

OTHER PUBLICATIONS

Chemical Abstracts Service, Dietmar Appelhans, et al., "Syntheses with aliphatic dialdehydes. Part 46. Synthesis and reactions of z,z-dialkyl-substituted malonaldehydes and their semiethylene acetalsl", pp. 2385-2392, Liebigs Annalen/Recueil (1997).*

Chemical Abstracts Service, Dietmar Appelhans, et al., "Syntheses with aliphatic dialdehydes. Part 46. Synthesis and reactions of 2,2-dialkyl-substituted malonaldehydes and their semi(ethylene acetals)", pp. 2385-2392, Liebigs Annalen/Recueil (1997).

Dietmar Appelhans, et al., "Syntheses with Aliphatic Dialdehydes, XLVI. Synthesis and Reactions of 2,2-Dialkyl-Substituted Malonaldehydes and Their Semi(Ethylene Acetals)," Liebigs Ann./Recueil (1997), pp. 2385-2392.

* cited by examiner

*Primary Examiner*—Kamal A. Saeed
*Assistant Examiner*—Janet L Coppins
(74) *Attorney, Agent, or Firm*—Sughrue Mion, PLLC

(57) ABSTRACT

A process for preparing intermediate compound (VII), compound (VIII) and compound (XIV) which will be raw materials for the synthesis of a synthetic antibactrial compound, via compound (I) or compound (X) and then, compound (II), the compounds each being shown below; and novel compounds useful for the preparation.

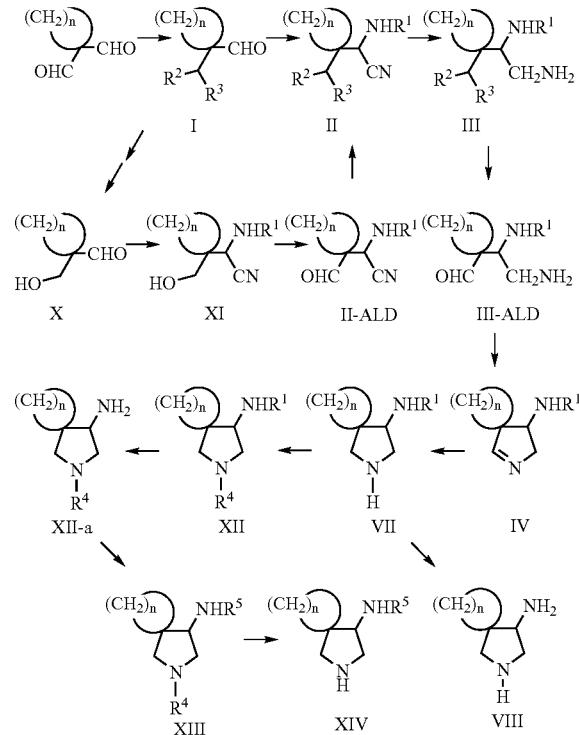

3 Claims, 6 Drawing Sheets

Figure 1A:
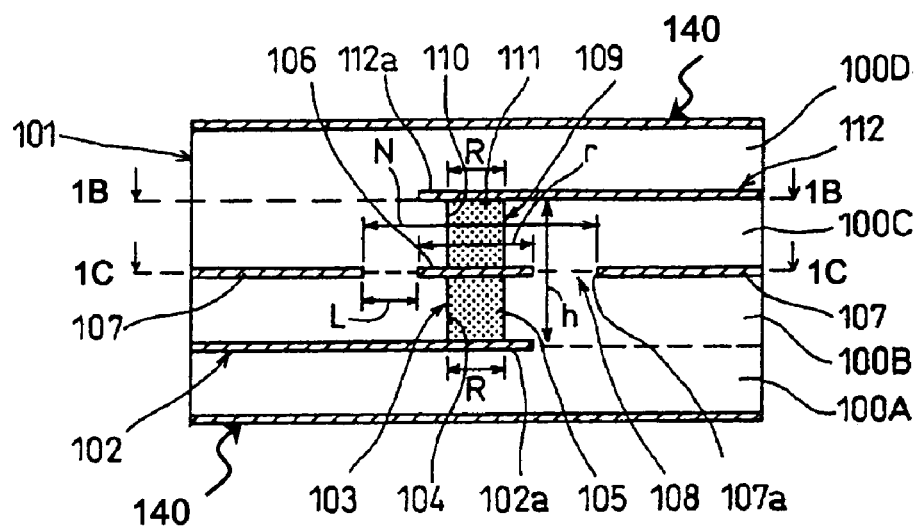
Figure 1B:
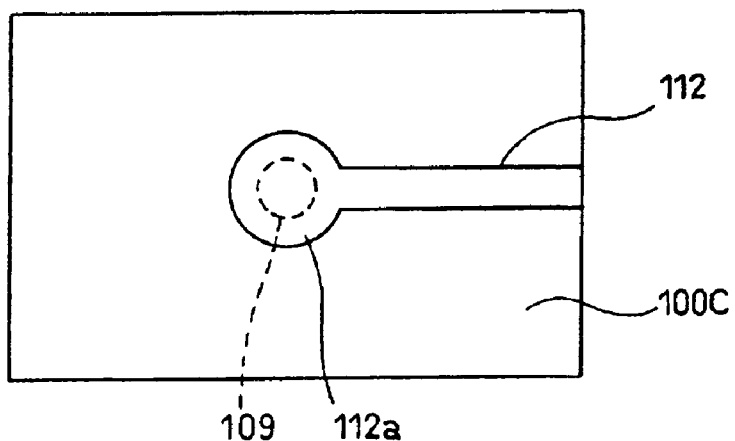
Figure 1C:
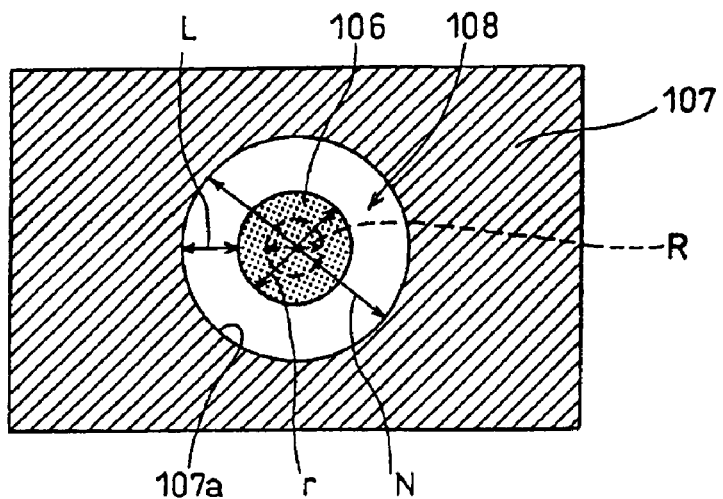
Figure 5A:
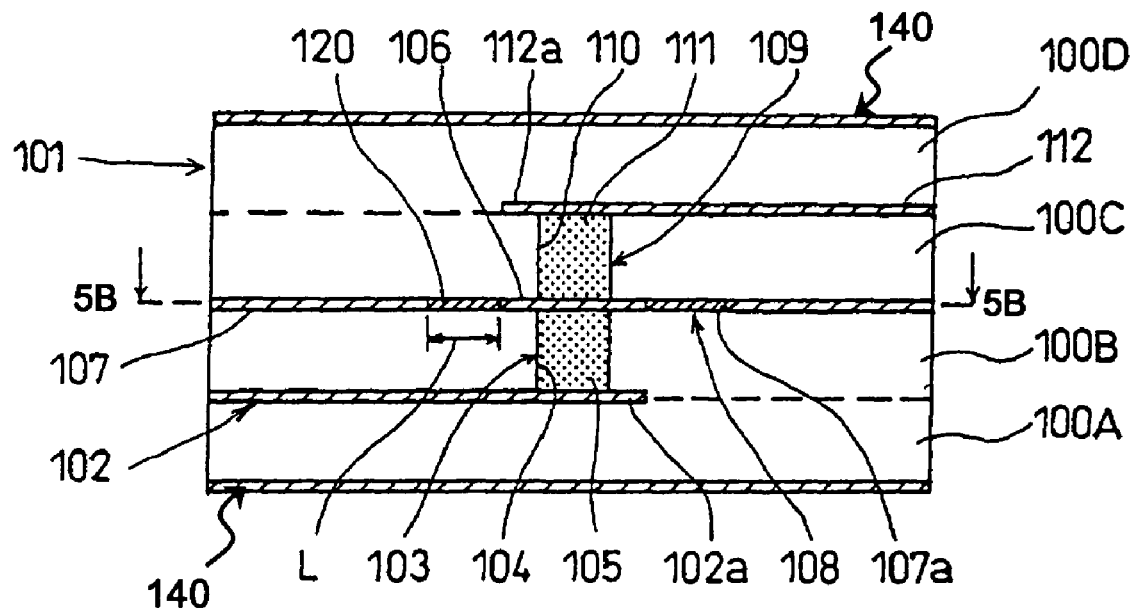
Figure 5B:
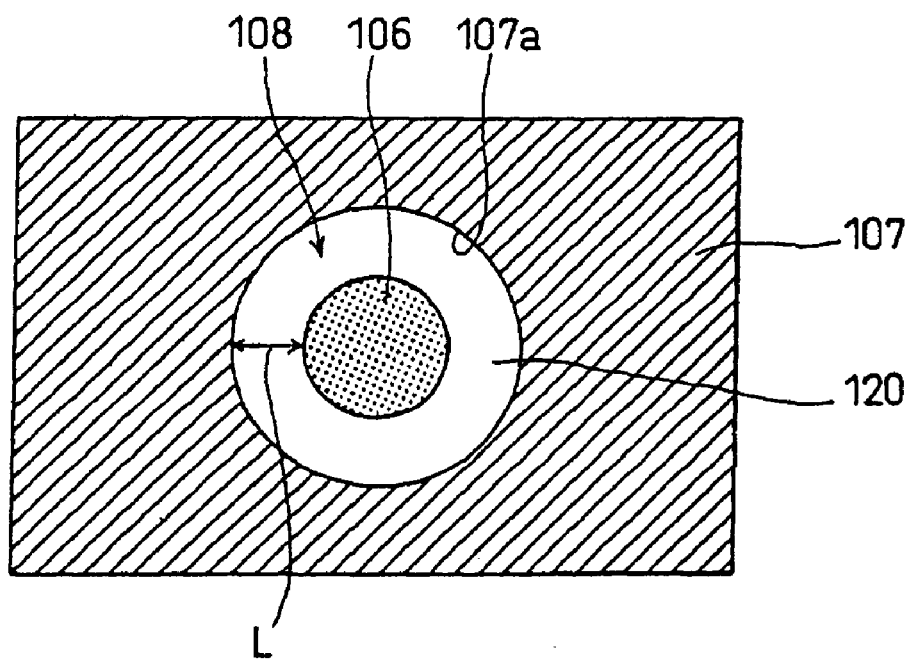
Figure 6A:
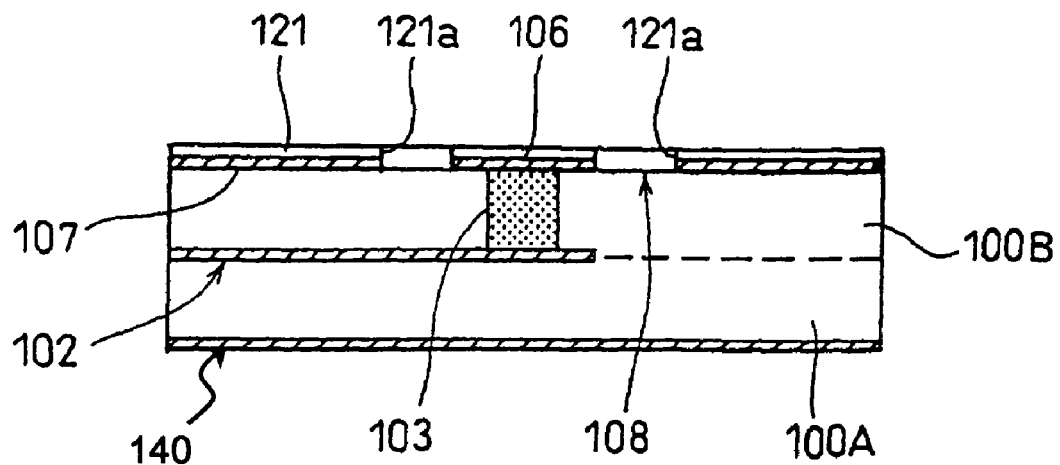
Figure 6B:
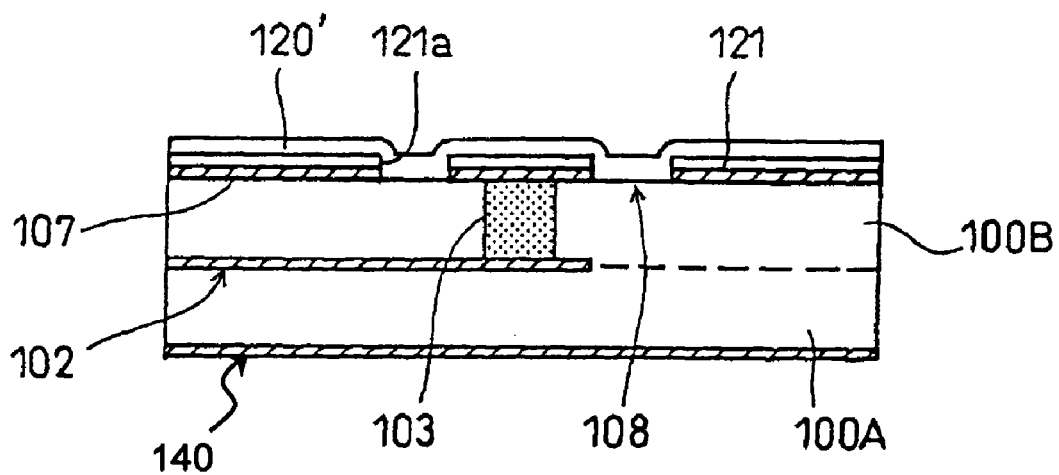
Figure 6C:
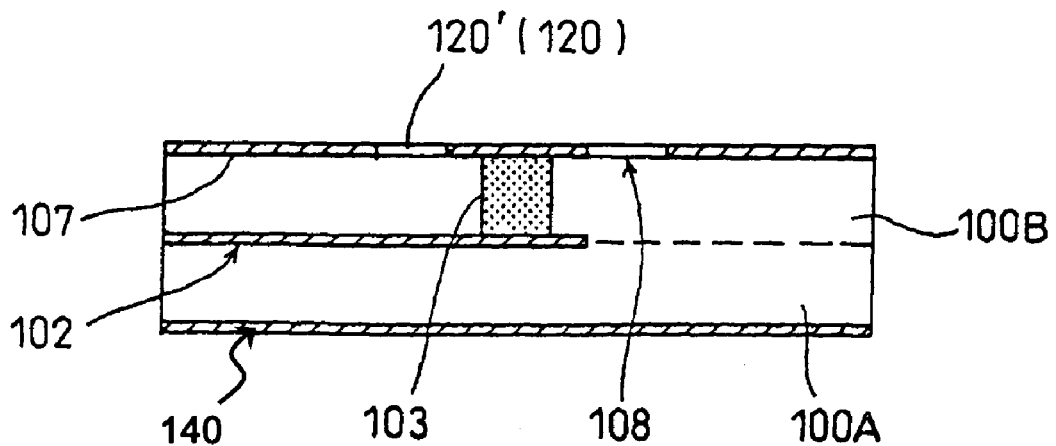
Figure 7A:
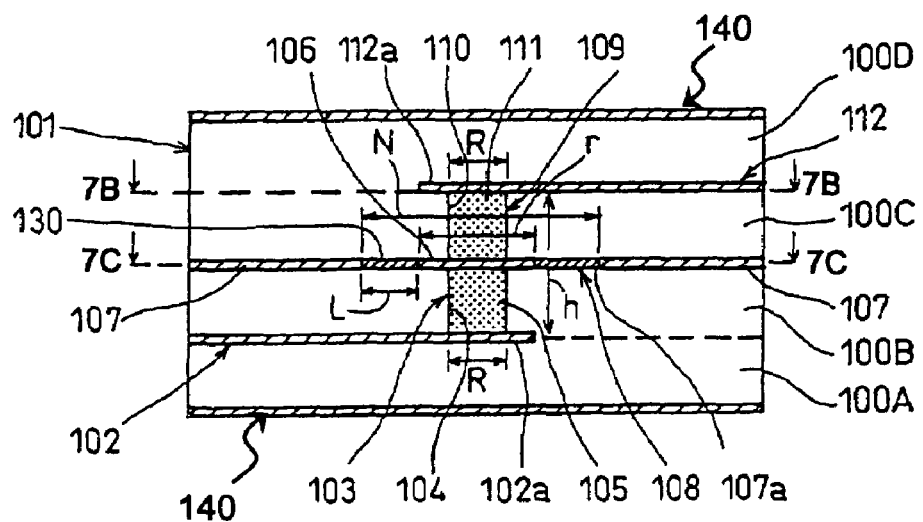
Figure 7B:
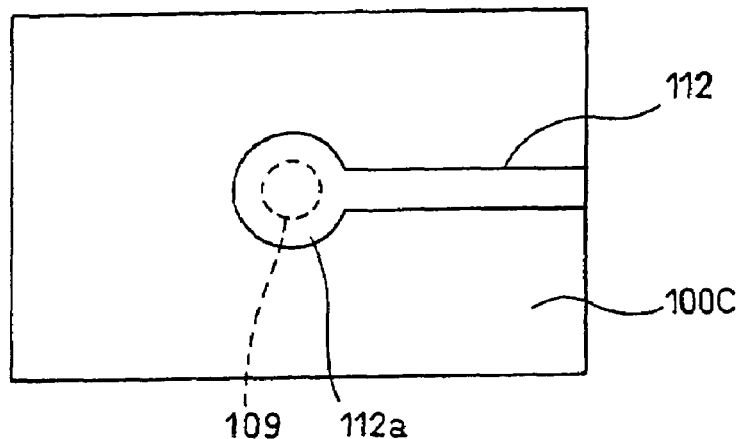
Figure 7C:
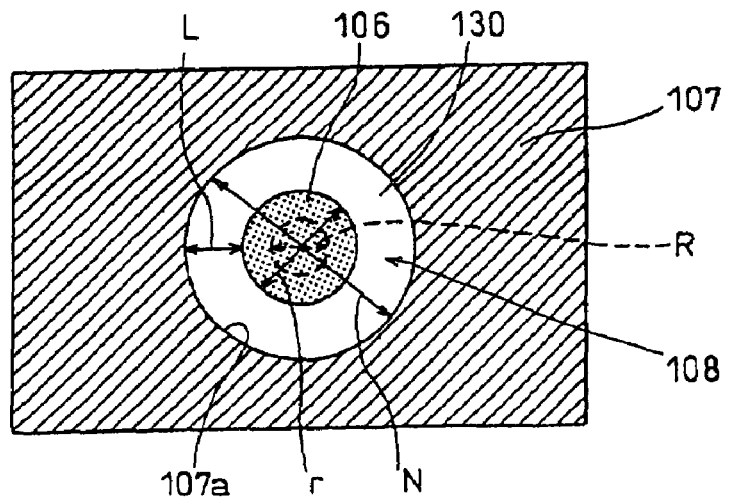
Figure 11:
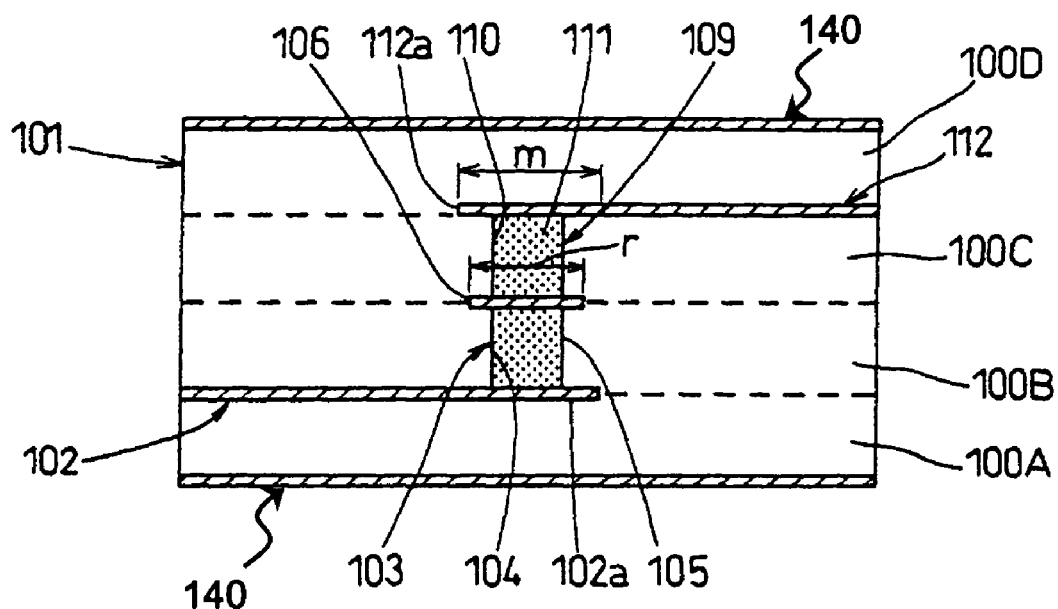
Figure 12:
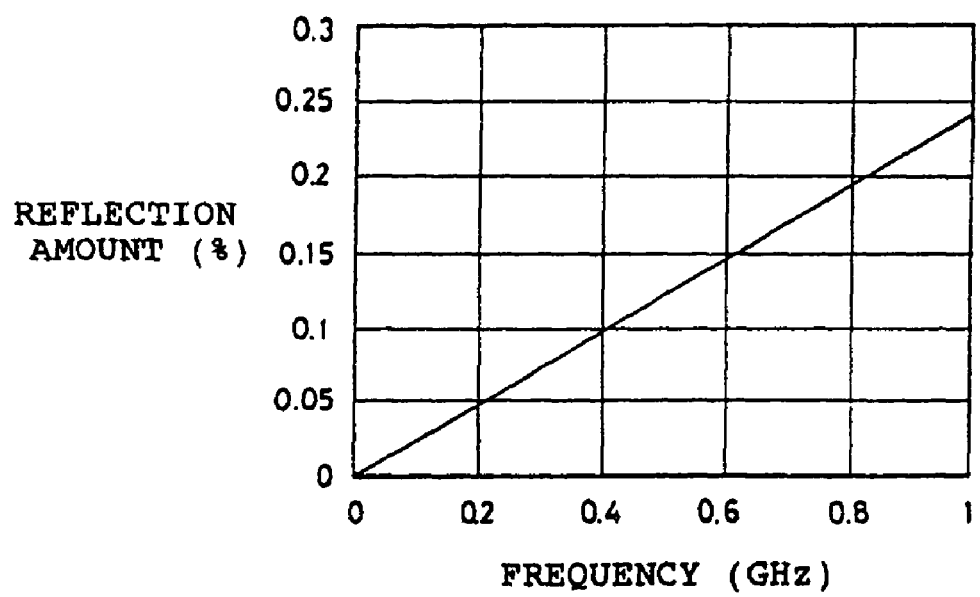

F I G. 9
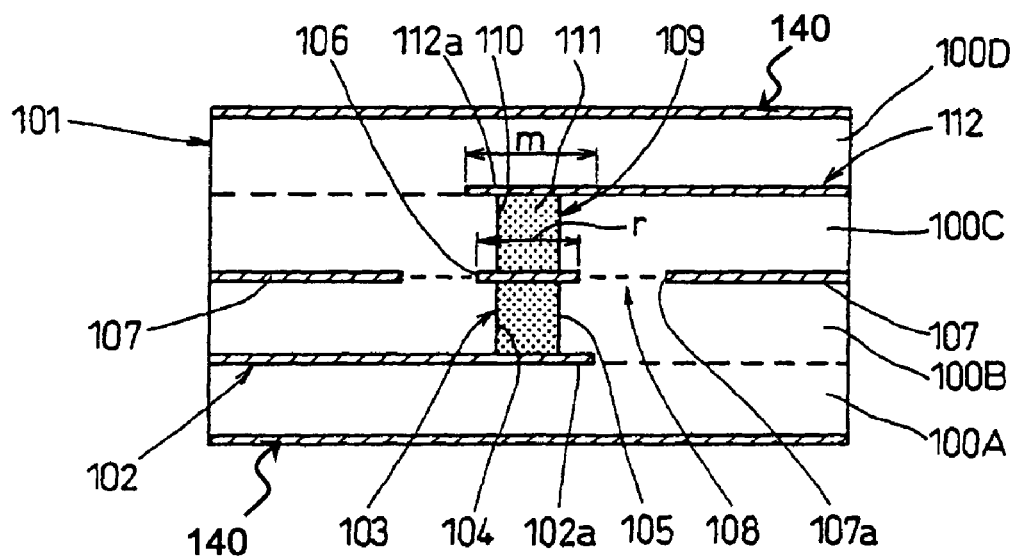
F I G. 1 0
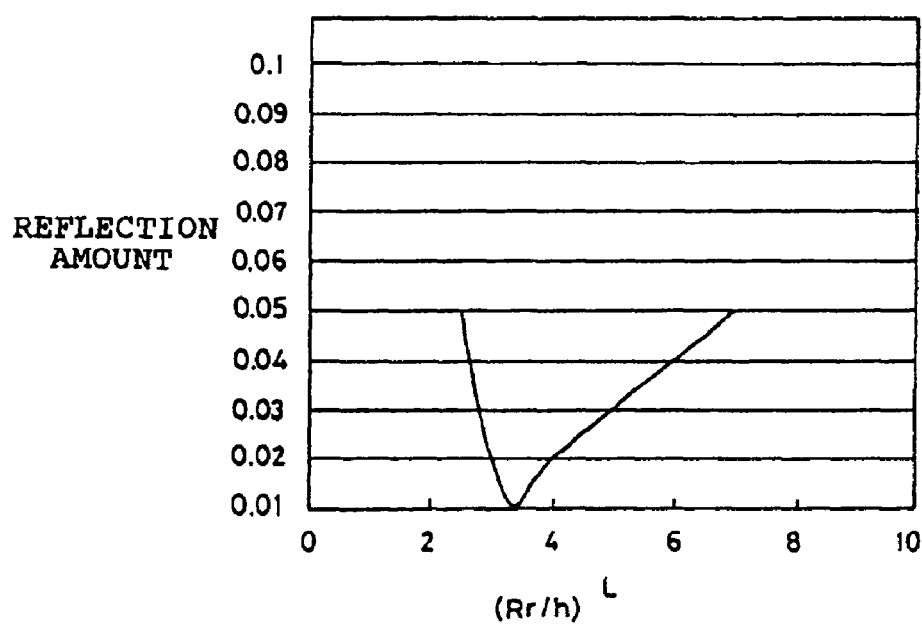

PROCESSES FOR PREPARATION OF BICYCLIC COMPOUNDS AND INTERMEDIATES THEREFOR

TECHNICAL FIELD

The present invention relates to novel processes for preparation of an amino-substituted azaspiroalkane compound having a spirocyclic structure, which compound is used as a raw material for the preparation of a quinolone derivative expected as an excellent antibacterial agent (JP-A-2-231475 and JP-A-3-95176, the term "JP-A" as used herein means an "unexamined published Japanese patent application"), and intermediate compounds useful for this preparation process.

BACKGROUND ART

A compound (amino-substituted azaspiroalkane) represented by formula (VIII):

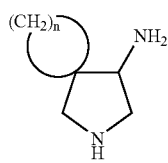

VIII (wherein, n stands for an integer of from 2 to 5) has been conventionally synthesized via a plurality of steps using ethyl acetoacetate as a starting material (JP-A-2-231475). An enantiomeric compound composed of a single isomer of the above-described compound has been so far prepared by converting a racemic modification of the compound into a diastereomer mixture having an optically active protecting group, separating a necessary isomer by preparative high performance liquid chromatography and then removing the protecting group (JP-A-3-95176). This process, however, needs a cumbersome operation and there was a room for improvement of it as an industrial process.

A preparation process utilizing the Strecker reaction or Dieckmann reaction was developed, but it is not industrially satisfactory, because a long reaction step is required for the conventional preparation process using such a reaction and in addition, asymmetric synthesis cannot be conducted readily.

An object of the present invention is to provide an industrially advantageous process for preparing, by convenient and short steps, an amino-substituted nitrogenous heterocyclic compound having a spirocyclic structure, particularly optically active amino-substituted [2.4]heptane derivative.

DISCLOSURE OF THE INVENTION

In view of the foregoing circumstances, the present inventors have found that from a compound represented by the following formula (particularly, a known compound in which n=2):

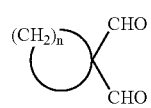

a compound represented by formula (I):

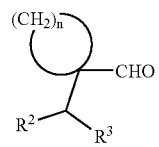

I and having one aldehyde group selectively acetalized can be prepared easily in a high yield and that the compound of the formula (I) can easily be converted into a compound represented by formula (II):

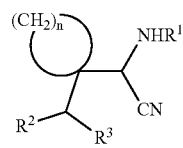

II

The present inventors have also found that the compound of the formula (II) is also easily available by oxidizing and acetalizing a compound represented by formula (XI):

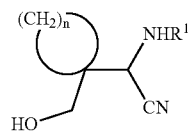

XI which compound can be easily obtained by the conversion of a compound represented by formula (X):

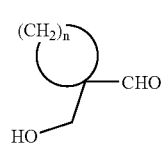

X

The present inventors have also found a process for preparing a compound represented by formula (VIII):

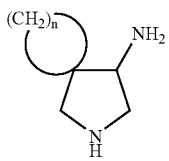

VIII by reducing the above-described compound of the formula (II) into a compound represented by formula (III):

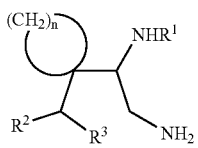

III

, and then preparing therefrom a compound represented by formula (IV):

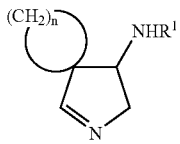

IV and then, a compound represented by formula (VII):

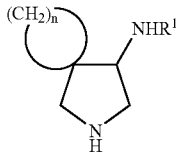

VII

The present inventors have also found a process for conveniently converting the protecting group of the amino group of the compound of the formula (VII) into another group.

In the compound of the formula (II), a carbon atom to which an amino group is bonded is an asymmetric carbon, meaning that when a substituent $R^1$ contains asymmetry, diastereomers exist. The present inventors have also found, upon preparation of the compound of the formula (II) which is a diastereomer mixture, a difference in a yield appears among the diastereomers and one diastereomer can be obtained preferentially compared with another diastereomer. They have found that this finding makes it possible to selectively obtain a necessary steroisomer.

Furthermore, the present inventors have found that when the compound of the formula (II) which is a diastereomer mixture is heated, particularly heated in a protonic solvent, epimerization of one diastereomer occurs, leading to preparation of a mixture preferentially containing another diastereomer. In other words, this isomerization makes it possible to convert an unnecessary steric compound into a necessary one, thereby attaining efficient preparation of the necessary stereoisomer.

Based on the above-described findings, the invention of the present application has been completed.

The present invention therefore relates to preparation processes which will be described below.

A process for preparing a compound represented by formula (VIII):

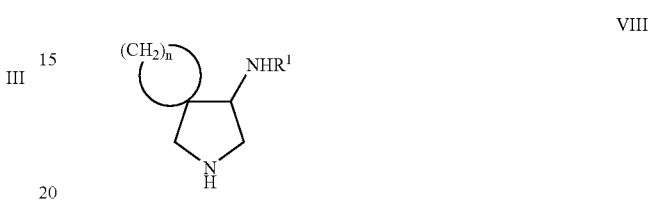

VIII

, or salt thereof, or a hydrate of the compound or salt, which comprises obtaining a compound represented by formula (II):

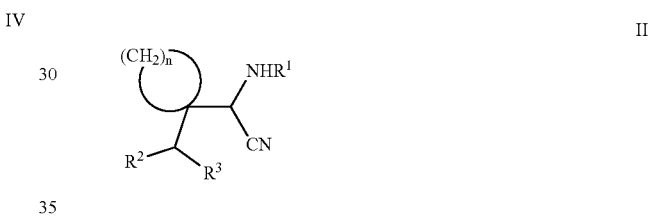

II by either one of Process A or B described below, reducing the cyano group of the resulting compound to prepare a compound represented by formula (III):

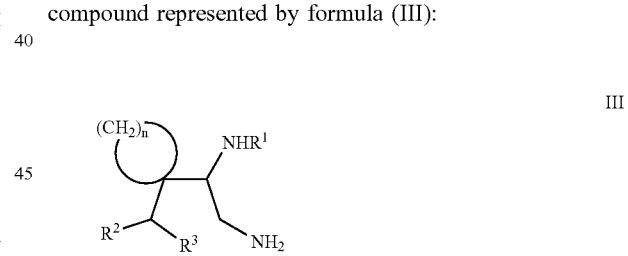

III

, hydrolyzing the resulting compound in the presence of an acid catalyst to prepare a compound represented by formula (III-ALD):

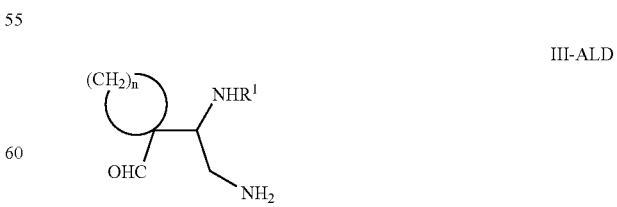

III-ALD

, subjecting the resulting compound to intramolecular ring-closure under neutral or basic conditions to prepare a compound represented by formula (IV):

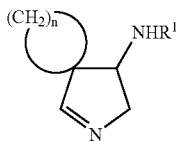

, reducing the resulting compound into a compound represented by formula (VII):

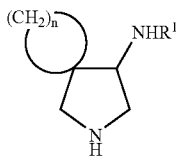

and, converting $R^1$ of the resulting compound into a hydrogen atom when the $R^1$ is not a hydrogen atom.

Process A:

A process of reacting a compound represented by formula:

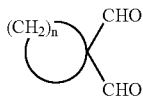

with an acetalization agent in the presence of an acid catalyst, and, if desired, in the presence of an additive, to prepare a compound represented by formula (I):

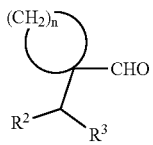

and reacting the resulting compound with a compound represented by formula (VI):

or salt thereof, and a cyanation agent.

Process B:

A process of reacting a compound represented by formula (X):

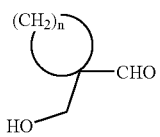

with a compound represented by formula (VI):

or salt thereof and a cyanation agent to prepare a compound represented by formula (XI):

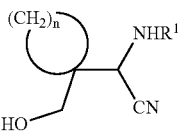

, oxidizing the resulting compound into a compound represented by formula (II-ALD):

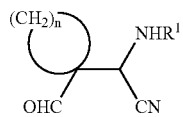

, and reacting the resulting compound with an acetalization agent in the presence of an acid catalyst, and if desired in the presence of an additive.

{In each of the above-described formulas, n stands for an integer of from 2 to 5, $R^1$ represents a hydrogen atom or a group represented by formula:

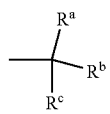

[wherein, $R^a$, $R^b$ and $R^c$ each independently represents a phenyl group, a benzyl group, a naphthyl group (the aryl portion of these groups may have one or more substituents, which may be the same or different in kind, selected from the class consisting of a $C_{1-4}$ alkyl group, a $C_{1-4}$ alkoxy group, a halogen atom and a nitro group), a hydrogen atom, or a $C_{1-4}$ alkyl group], and $R^2$ and $R^3$ each independently represents a $C_{1-4}$ alkoxy group or may be integrated together to form a group represented by formula:

(wherein, m stands for an integer of from 1 to 4)};

the above-described preparation process, wherein the compound represented by the formula (II) is prepared by Process A;

the above-described preparation process, wherein the compound represented by the formula (II) is prepared by Process B;

the above-described preparation process, wherein the cyano group is reduced using catalytic hydrogenation reaction or a metal hydride;

the above-described preparation process, wherein the cyano group is reduced using catalytic hydrogenation reaction;

the above-described preparation process, wherein the acid catalyst is hydrochloric acid;

the above-described preparation process, wherein the ring-closure reaction is conducted under neutral or basic conditions;

the above-described preparation process, wherein $R^2$ and $R^3$ each represents a $C_{1-4}$ alkoxy group;

the above-described preparation process, wherein $R^2$ and $R^3$ each represents an ethoxy group;

the above-described preparation process, wherein the compound represented by the formula (IV) is reduced using catalytic hydrogenation reaction or a metal hydride;

the above-described preparation process, wherein the compound of the formula (IV) is reduced using catalytic hydrogenation reaction;

the above-described preparation process, wherein the catalyst is Raney nickel or Raney cobalt;

a process for preparing a compound represented by formula (VIII):

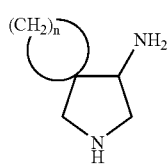

VIII or salt thereof, which comprises:

reacting a compound represented by formula (I):

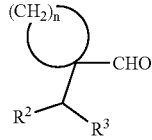

I with a compound represented by formula (VI):

H$_2$N—R$^1$

VI or salt thereof and a cyanation agent to prepare a compound represented by formula (II):

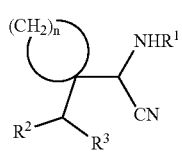

II

, reducing the cyano group of the resulting compound to prepare a compound represented by formula (III):

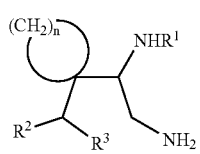

III

, hydrolyzing the resulting compound in the presence of an acid catalyst to prepare a compound represented by formula (III-ALD):

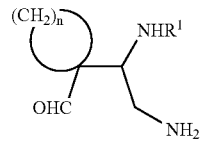

III-ALD

, subjecting the resulting compound to intramolecular ring-closure under neutral or basic conditions to prepare a compound represented by formula (IV):

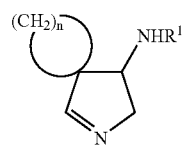

IV

, reducing the compound into a compound represented by formula (VII):

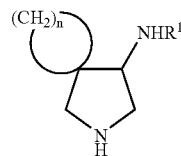

VII and, converting $R^1$ of the resulting compound into a hydrogen atom when the $R^1$ is not a hydrogen atom {in each of the above-described formulas, n stands for an integer of from 2 to 5, $R^1$ represents a hydrogen atom or a group represented by formula:

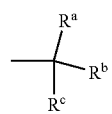

[wherein, $R^a$, $R^b$ and $R^c$ each independently represents a phenyl group, a benzyl group, a naphthyl group (the aryl portion of these groups may have one or more substituents, which may be the same or different in kind, selected from the class consisting of a $C_{1-4}$ alkyl group, a $C_{1-4}$ alkoxy group, a halogen atom and a nitro group), a hydrogen atom, or a $C_{1-4}$ alkyl group], and $R^2$ and $R^3$ each independently represents a $C_{1-4}$ alkoxy group or may be integrated together to form a group represented by formula:

—O—(CH$_2$)$_m$—O—

(wherein, m stands for an integer of from 1 to 4)};

the above-described preparation process, wherein the compound represented by the formula (I) is a compound represented by formula (I-R):

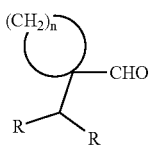

I-R (wherein, R represents a $C_{1-4}$ alkoxy group and n stands for an integer of from 2 to 5);

the above-described preparation process, wherein the compound represented by the formula (I-R) is available by reacting a compound represented by formula:

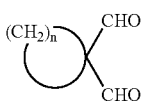

(wherein, n stands for an integer of from 2 to 5) with an acetalization agent in the presence of an acid catalyst and if desired, in the presence of an additive;

the above-described preparation process, wherein the compound represented by the formula (I-R) is available by reacting a compound represented by formula:

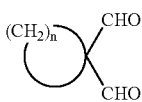

(wherein, n stands for an integer of from 2 to 5) with a compound represented by formula:

HC(R)$_3$ (wherein, R represents a $C_{1-4}$ alkoxy group) in the presence of an acid catalyst;

the above-described preparation process, wherein the additive is a compound represented by formula:

HC(R)$_3$ (wherein, R represents a $C_{1-4}$ alkoxy group) or a dehydrating agent;

the above-described preparation process, wherein the compound represented by the formula (I-R) is available by reacting a compound represented by formula:

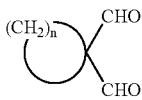

(wherein, n stands for an integer of from 2 to 5) with a compound represented by formula:

HR (wherein, R represents a $C_{1-4}$ alkoxy group) in the presence of an acid catalyst and a dehydrating agent serving as an additive;

the above-described preparation process, wherein the dehydrating agent is an anhydride of an inorganic salt, the above-described preparation process, wherein the dehydrating agent is anhydrous magnesium sulfate or anhydrous sodium sulfate;

the above-described preparation process, wherein the compound represented by the formula (I-R) is available by reacting a compound represented by formula:

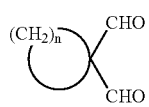

with a compound represented by formula:

HR (wherein, R represents a $C_{1-4}$ alkoxy group) in the presence of an acid catalyst and a catalytic amount of a compound represented by formula:

HC(R)$_3$ (wherein, R represents a $C_{1-4}$ alkoxy group) which compound serves as the additive;

the above-described preparation process, wherein the acid catalyst is a sulfonic acid compound;

the above-described preparation process, wherein R represents an ethoxy group;

the above-described preparation process, wherein the cyanation agent is hydrogen cyanide or acetone cyanhydrin;

the above-described preparation process, wherein the cyanation agent is hydrogen cyanide;

the above-described preparation process, wherein the cyanation agent is acetone cyanhydrin;

the above-described preparation process, wherein the cyano group of the compound represented by the formula (II) is reduced by catalytic hydrogenation;

the above-described preparation process, wherein the compound represented by the formula (IV) is reduced by a metal hydride compound or catalytic hydrogenation;

a process for preparing a compound represented by formula (I):

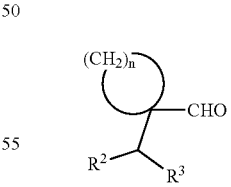

I

{wherein, n stands for an integer of from 2 to 5,

R$^2$ and R$^3$ each independently represents a $C_{1-4}$ alkoxy group or may be integrated together to form a group represented by formula:

—O—(CH$_2$)$_m$—O—

(wherein, m stands for an integer of from 1 to 4)}, which comprises reacting a compound of formula:

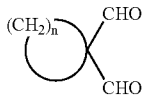

(wherein, n stands for an integer of from 2 to 5) with an acetalization agent in the presence of an acid catalyst and, if desired, in the presence of an additive;

the above-described preparation process, wherein $R^2$ and $R^3$ each independently represents a $C_{1-4}$ alkoxy group;

the above-described preparation process, wherein the compound of the formula (I) is available by reacting a compound represented by formula:

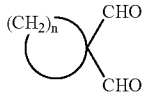

(wherein, n stands for an integer of from 2 to 5) with a compound of formula:

$HC(R)_3$ (wherein, R represents a $C_{1-4}$ alkoxy group) in the presence of an acid catalyst;

the above-described preparation process, wherein the additive is a compound represented by formula:

$HC(R)_3$ (wherein, R represents a $C_{1-4}$ alkoxy group) or a dehydrating agent;

the above-described preparation process, wherein the compound represented by the formula (I) is available by reacting a compound represented by formula:

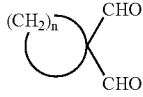

(wherein, n stands for an integer of from 2 to 5) with a compound represented by formula:

HR (wherein, R represents a $C_{1-4}$ alkoxy group) in the presence of an acid catalyst and a dehydrating agent serving as an additive;

the above-described preparation process, wherein the dehydrating agent is an anhydride of an inorganic salt, the above-described preparation process, wherein the dehydrating agent is anhydrous magnesium sulfate or anhydrous sodium sulfate;

the above-described preparation process, wherein the compound represented by the formula (I) is available by reacting a compound represented by formula:

with a compound represented by formula:

HR (wherein, R represents a $C_{1-4}$ alkoxy group) in the presence of an acid catalyst and a catalytic amount of a compound represented by formula:

$HC(R)_3$ (wherein, R represents a $C_{1-4}$ alkoxy group) which compound serves as the additive;

the above-described preparation process, wherein the acid catalyst is a sulfonic acid compound;

the above-described preparation process, wherein R represents an ethoxy group;

a process for preparing a compound represented by formula (II):

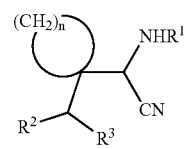

[wherein, n stands for an integer of from 2 to 5, $R^1$ represents a hydrogen atom or a group represented by formula:

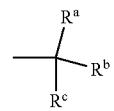

[wherein, $R^a$, $R^b$ and $R^c$ each independently represents a phenyl group, a benzyl group, a naphthyl group (the aryl portion of these groups may have one or more substituents, which may be the same or different in kind, selected from the class consisting of a $C_{1-4}$ alkyl group, a $C_{1-4}$ alkoxy group, a halogen atom and a nitro group), a hydrogen atom, or a $C_{1-4}$ alkyl group], and $R^2$ and $R^3$ each independently represents a $C_{1-4}$ alkoxy group or may be integrated together to form a group represented by the formula:

$$—O—(CH_2)_m—O—$$

(wherein, m stands for an integer of from 1 to 4)], which comprises reacting a compound represented by formula (I):

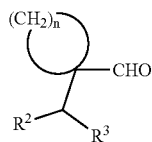

[wherein, n, $R^2$ and $R^3$ have the same meanings as described above] with a compound represented by the formula (VI):

(wherein, $R^1$ has the same meaning as described above), or salt thereof and a cyanation agent;

the above-described preparation process, wherein the cyanation agent is hydrogen cyanide or acetone cyanhydrin;

the above-described preparation process, wherein the cyanation agent is hydrogen cyanide;

the above-described preparation process, wherein the cyanation agent is acetone cyanhydrin;

A process for preparing a compound represented by formula (II):

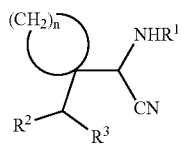

{wherein, n stands for an integer of from 2 to 5, $R^1$ represents a hydrogen atom or a group represented by formula:

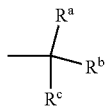

[wherein, $R^a$, $R^b$ and $R^c$ each independently represents a phenyl group, a benzyl group, a naphthyl group (the aryl portion of these groups may have one or more substituents, which may be the same or different in kind, selected from the class consisting of a $C_{1-4}$ alkyl group, a $C_{1-4}$ alkoxy group, a halogen atom and a nitro group), a hydrogen atom, or a $C_{1-4}$ alkyl group], and $R^2$ and $R^3$ each independently represents a $C_{1-4}$ alkoxy group or may be integrated together to form a group represented by formula:

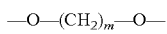

(wherein, m stands for an integer of from 1 to 4)}, which comprises reacting a compound represented by formula (X):

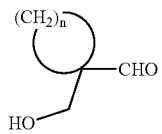

with a compound represented by formula (VI):

or salt thereof and a cyanation agent to prepare a compound of formula (XI):

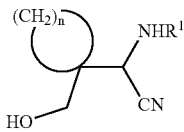

, oxidizing the resulting compound into a compound represented by formula (II-ALD):

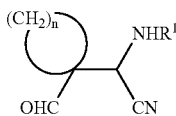

, and reacting the resulting compound with an acetalization agent in the presence of an acid catalyst and if desired, in the presence of an additive;

the above-described preparation process, wherein the oxidant is a Collins reagent, pyridinium chlorochromate, pyridinium dichromate, Dess-Martin, or Periodinane;

the above-described preparation process, wherein the oxidant is pyridinium chlorochromate;

the above-described preparation process, wherein the compound represented by the formula (II) is a compound represented by formula (II-R):

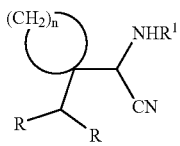

{wherein, n stands for an integer of from 2 to 5, $R^1$ represents a hydrogen atom or a group represented by formula:

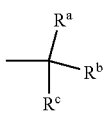

[wherein, $R^a$, $R^b$ and $R^c$ each independently represents a phenyl group, a benzyl group, a naphthyl group (the aryl portion of these groups may have one or more substituents, which may be the same or different in kind, selected from the class consisting of a $C_{1-4}$ alkyl group, a $C_{1-4}$ alkoxy groups, a halogen atom and a nitro group), a hydrogen atom, or a $C_{1-4}$ alkyl group], and R represents a $C_{1-4}$ alkoxy group};

the above-described preparation process, wherein the compound represented by the formula (II-R) is a compound available by reacting a compound represented by formula (II-ALD):

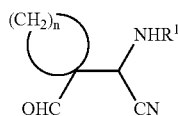

II-ALD with a compound represented by formula:

HC(R)$_3$ (wherein, R represents a $C_{1-4}$ alkoxy group) in the presence of an acid catalyst;

the above-described preparation process, wherein R is an ethoxy group;

the above-described preparation process, wherein the acid catalyst is a sulfonic acid compound;

the above-described preparation process, wherein the cyanation agent is hydrogen cyanide or acetone cyanhydrin;

the above-described preparation process, wherein the cyanation agent is hydrogen cyanide;

the above-described preparation process, wherein $R^1$ is a group represented by formula:

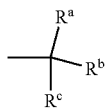

[wherein, $R^a$, $R^b$ and $R^c$ each independently represents a phenyl group, a benzyl group, a naphthyl group (the aryl portion of these groups may have one or more substituents, which may be the same or different in kind, selected from the class consisting of a $C_{1-4}$ alkyl group, a $C_{1-4}$ alkoxy group, a halogen atom and a nitro group), a hydrogen atom, or a $C_{1-4}$ alkyl group];

a process for preparing a compound represented by formula (III):

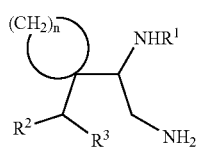

III

[wherein, n stands for an integer of from 2 to 5, $R^1$ represents a hydrogen atom or a group represented by formula:

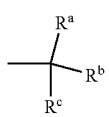

[wherein, $R^a$, $R^b$ and $R^c$ each independently represents a phenyl group, a benzyl group, a naphthyl group (the aryl portion of these groups may have one or more substituents, which may be the same or different in kind, selected from the class consisting of a $C_{1-4}$ alkyl group, a $C_{1-4}$ alkoxy group, a halogen atom and a nitro group), a hydrogen atom, or a $C_{1-4}$ alkyl group], and $R^2$ and $R^3$ each independently represents a $C_{1-4}$ alkoxy group or may be integrated together to form a group represented by the formula:

—O—(CH$_2$)$_m$—O—

(wherein, m stands for an integer of from 1 to 4)}, which comprises reducing the cyano group of a compound represented by formula (II):

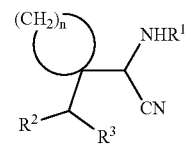

II

{wherein, n, $R^1$, $R^2$ and $R^3$ have the same meanings as described above} or salt thereof;

the above-described preparation process, wherein the reduction is conducted using catalytic hydrogenation reaction or a metal hydride;

the above-described preparation process, wherein the reduction is conducted using catalytic hydrogenation reaction;

the above-described preparation process, wherein the compound represented by the formula (III) is a stereochemically single compound;

the above-described preparation process, wherein the compound represented by the formula (III) is a compound having a configuration of the following formula:

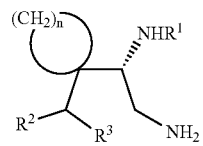

(wherein, n, $R^1$, $R^2$ and $R^3$ have the same meanings as described above);

a process for preparing a compound represented by formula (IV):

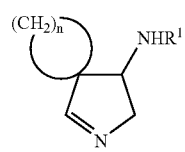

IV

[wherein, n stands for an integer of from 2 to 5, and $R^1$ represents a hydrogen atom or a group represented by formula:

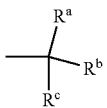

[wherein, $R^a$, $R^b$ and $R^c$ each independently represents a phenyl group, a benzyl group, a naphthyl group (the aryl portion of these groups may have one or more substituents, which may be the same or different in kind, selected from the class consisting of a $C_{1-4}$ alkyl group, a $C_{1-4}$ alkoxy group, a halogen atom and a nitro group), a hydrogen atom, or a $C_{1-4}$ alkyl group], which comprises subjecting, to a ring-closure, a compound represented by formula (III):

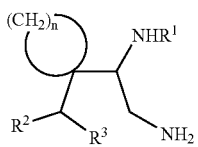

III

{wherein, n and $R^1$ have the same meanings as described above, and $R^2$ and $R^3$ each independently represents a $C_{1-4}$ alkoxy group, or may be integrated together to form a group represented by formula:

—O—$(CH_2)_m$—O—

(wherein, m stands for an integer of from 1 to 4)}, or salt thereof;

the above-described preparation process, wherein the compound represented by the formula (III) is hydrolyzed in the presence of an acid catalyst, followed by ring closure of the resulting hydrolyzate;

the above-described preparation process, wherein the hydrolyzate is a compound represented by formula (III-ALD):

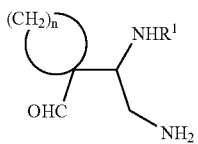

III-ALD

{wherein, n stands for an integer of from 2 to 5, and $R^1$ represents a hydrogen atom or a group represented by formula:

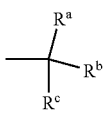

[wherein, $R^a$, $R^b$ and $R^c$ each independently represents a phenyl group, a benzyl group, a naphthyl group (the aryl portion of these groups may have one or more substituents, which may be the same or different in kind, selected from the class consisting of a $C_{1-4}$ alkyl group, a $C_{1-4}$ alkoxy group, a halogen atom and a nitro group), a hydrogen atom, or a $C_{1-4}$ alkyl group]};

the above-described preparation process, wherein the acid catalyst is hydrochloric acid;

the above-described preparation process, wherein the ring-closure reaction is conducted under neutral or basic conditions;

the above-described preparation process, wherein the compound represented by the formula (IV) is a stereochemically single compound;

the above-described preparation process, wherein the compound represented by the formula (IV) has a configuration of the following formula:

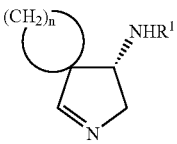

(wherein, n and $R^1$ have the same meanings as described above);

the above-described preparation process, wherein $R^2$ and $R^3$ each represents a $C_{1-4}$ alkoxy group:

the above-described preparation process, wherein $R^2$ and $R^3$ each represents an ethoxy group;

a process for preparing a-compound represented by formula (VII):

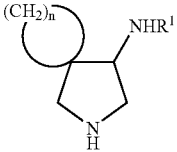

VII

{wherein, n stands for an integer of from 2 to 5, $R^1$ represents a hydrogen atom or a group represented by formula:

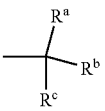

[wherein, $R^a$, $R^b$ and $R^c$ each independently represents a phenyl group, a benzyl group, a naphthyl group (the aryl portion of these groups may have one or more substituents, which may be the same or different in kind, selected from the class consisting of a $C_{1-4}$ alkyl group, a $C_{1-4}$ alkoxy group, a halogen atom and a nitro group), a hydrogen atom, or a $C_{1-4}$ alkyl group], and $R^2$ and $R^3$ have the same meanings as described above}, which comprises reducing a compound represented by formula (IV):

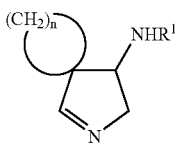

IV

[wherein, n and $R^1$ have the same meanings as described above];

the above-described preparation process, wherein the reduction is conducted using catalytic hydrogenation reaction or a metal hydride;

the above-described preparation process, wherein the reduction is conducted using catalytic hydrogenation reaction;

the above-described preparation process, wherein the catalyst is Raney nickel;

the above-described preparation process, wherein the compound represented by the formula (VII) is a stereochemically single compound;

the above-described preparation process, wherein the compound represented by the formula (VII) has a configuration of the following formula:

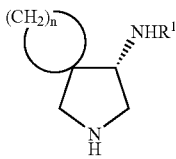

(wherein, n and $R^1$ have the same meanings as described above);

a process for preparing an isomer mixture, which comprises treating a mixture of isomers which are based on asymmetry of a carbon atom to which bonded is the cyano group of a compound represented by formula (II):

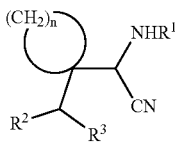

II

{wherein, n stands for an integer of from 2 to 5, $R^1$ represents a hydrogen atom or a group represented by formula:

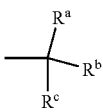

[wherein, $R^a$, $R^b$ and $R^c$ each independently represents a phenyl group, a benzyl group, a naphthyl group (the aryl portion of these groups may have one or more substituents, which may be the same or different in kind, selected from the class consisting of a $C_{1-4}$ alkyl group, a $C_{1-4}$ alkoxy group, a halogen atom and a nitro group), a hydrogen atom, or a $C_{1-4}$ alkyl group], and $R^2$ and $R^3$ each independently represents a $C_{1-4}$ alkoxy group or may be integrated together to form a group represented by formula:

$$-O-(CH_2)_m-O-$$

(wherein, m stands for an integer of from 1 to 4)}, and which mixture contains one of the isomers represented by formula:

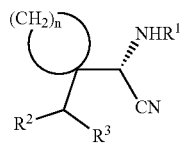

(wherein, n, $R^1$, $R^2$ and $R^3$ have the same meanings as defined above) in a smaller amount than another isomer, thereby making the content of the former isomer greater than the content of the latter isomer;

the above-described preparation process, wherein the treatment is heating;

the above-described preparation process, wherein the treatment is heating in a polar solvent;

the above-described preparation process, wherein the polar solvent is an alcohol;

the above-described preparation process, wherein the alcohol is ethanol;

a process for preparing an isomer compound represented by formula:

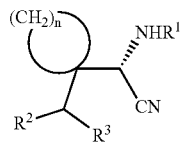

{wherein, n stands for an integer of from 2 to 5, $R^1$ represents a hydrogen atom or a group represented by formula:

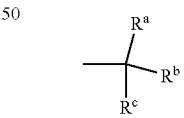

[wherein, $R^a$, $R^b$ and $R^c$ each independently represents a phenyl group, a benzyl group, a naphthyl group (the aryl portion of these groups may have one or more substituents, which may be the same or different in kind, selected from the class consisting of a $C_{1-4}$ alkyl group, a $C_{1-4}$ alkoxy group, a halogen atom and a nitro group), a hydrogen atom, or a $C_{1-4}$ alkyl group, and $R^2$ and $R^3$ each independently represents a $C_{1-4}$ alkoxy group or may be integrated together to form a group represented by formula:

$$-O-(CH_2)_m-O-$$

(wherein, m stands for an integer of from 1 to 4)}, which comprises reacting a compound represented by formula (I):

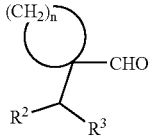

I

[wherein, n, $R^2$ and $R^3$ have the same meanings as described above] with a compound represented by formula (VI):

VI (wherein, $R^1$ has the same meaning as described above) or salt thereof, and a cyanation agent, separating, from the resulting compound represented by formula (II):

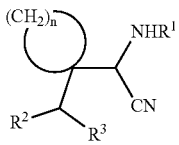

II (wherein, n, $R^1$, $R^2$ and $R^3$ have the same meanings as described above), an isomer compound represented by formula:

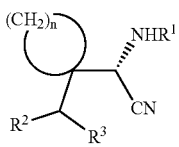

[wherein, n, $R^1$, $R^2$ and $R^3$ have the same meanings as described above], and isomerizing another isomer compound which is represented by the following formula:

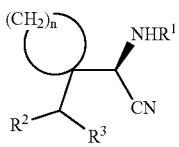

[wherein, n, $R^1$, $R^2$ and $R^3$ have the same meanings as defined above] and has remained after separation;
the above-described preparation process, wherein the reaction is effected in an alcohol;
the above-described preparation process, wherein the cyanation agent is hydrogen cyanide or acetone cyanhydrin;
the above-described preparation process, wherein the cyanation agent is hydrogen cyanide;
the above-described preparation process, wherein the cyanation agent is acetone cyanhydrin;
the above-described preparation process, wherein the isomer compound represented by formula:

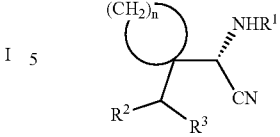

[wherein n, $R^1$, $R^2$ and $R^3$ have the same meanings as described above] is separated from the compound represented by formula (II):

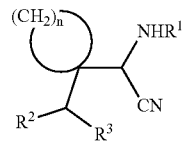

II

[wherein n, $R^1$, $R^2$ and $R^3$ have the same meanings as described above] by adding water to the reaction mixture, thereby precipitating the isomer;
the above-described preparation process, wherein the isomerization of the remaining isomer compound represented by formula:

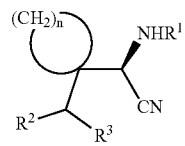

[wherein n, $R^1$, $R^2$ and $R^3$ have the same meanings as described above] is effected by heating;
the above-described preparation process, wherein n stands for 2;
the above-described preparation process, wherein $R^a$, $R^b$ and $R^c$ each represents a group selected from the class consisting of methyl, ethyl, phenyl, 4-methylphenyl, 4-methoxyphenyl, 4-chlorophenyl, 4-nitrophenyl, 2,4-dichlorophenyl, 2,4-dinitrophenyl, 3,5-dichlorophenyl, 3,5-dinitrophenyl and naphthyl groups;
the above-described preparation process, wherein $R^a$, $R^b$ and $R^c$ represent different groups each other;
the above-described preparation process, wherein the substituent $R^1$ is a group selected from the class consisting of (R)-1-phenylethyl, (S)-1-phenylethyl, (R)-1-phenylpropyl, (S)-1-phenylpropyl, (R)-1-phenyl-2-(p-tolyl)ethyl, (S)-1-phenyl-2-(p-tolyl)ethyl, (R)-1-(1-naphthyl)ethyl, (S)-1-(1-naphthyl)ethyl, (R)-1-(4-methoxyphenyl)ethyl, (S)-1-(4-methoxyphenyl)ethyl, (R)-1-(4-chlorophenyl)ethyl, (S)-1-(4-chlorophenyl)ethyl, (R)-1-(4-nitrophenyl)ethyl, (S)-1-(4-nitrophenyl)ethyl, (R)-1-(2,4-dichlorophenyl)ethyl, (S)-1-(2,4-dichlorophenyl)ethyl, (R)-1-(2,4-dinitrophenyl)ethyl, (S)-1-(2,4-dinitrophenyl)ethyl, (R)-1-(3,5-dichlorophenyl)ethyl, (S)-1-(3,5-dichlorophenyl)ethyl, (R)-1-(3,5-dinitrophenyl)ethyl, and (S)-1-(3,5-dinitrophenyl)ethyl groups;
the above-described preparation process, wherein the substituent $R^1$ is an (R)-1-phenylethyl or (S)-1-phenylethyl group; and the like.

In addition, the invention of the present application relates to the following compounds.

A compound represented by formula (I):

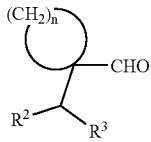

I

{wherein, n stands for an integer of from 2 to 5, $R^2$ and $R^3$ each independently represents a $C_{1-4}$ alkoxy group or may be integrated together to form a group represented by formula:

(wherein, m stands for an integer of from 1 to 4)};

the above-described compound, wherein $R^2$ and $R^3$ each represents a $C_{1-4}$ alkoxy group;

the above-described compound, wherein $R^2$ and $R^3$ each represents an ethoxy group;

a compound represented by formula (II):

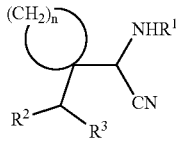

II

[wherein, n stands for an integer of from 2 to 5, $R^1$ represents a hydrogen atom or a group represented by formula:

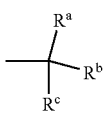

[wherein, $R^a$, $R^b$ and $R^c$ each independently represents a phenyl group, a benzyl group, a naphthyl group (the aryl portion of these groups may have one or more substituents, which may be the same or different in kind, selected from the class consisting of a $C_{1-4}$ alkyl group, a $C_{1-4}$ alkoxy group, a halogen atom and a nitro group), a hydrogen atom, or a $C_{1-4}$ alkyl group], and $R^2$ and $R^3$ each independently represents a $C_{1-4}$ alkoxy group or may be integrated together to form a group represented by formula:

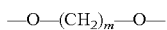

(wherein, m stands for an integer of from 1 to 4)}, or salt thereof, or a hydrate of the compound or salt;

the above-described compound, wherein the compound represented by the formula (II) has a configuration of the following formula:

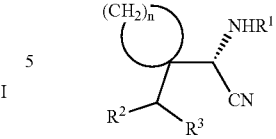

(wherein, n, $R^1$, $R^2$ and $R^3$ have the same meanings as described above), or salt thereof, or the hydrate of the compound or salt;

a compound represented by formula (II-AD):

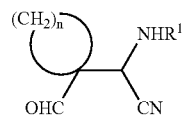

II-ALD

{wherein, n stands for an integer of from 2 to 5, and $R^1$ represents a hydrogen atom or a group represented by formula:

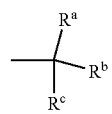

[wherein, $R^a$, $R^b$ and $R^c$ each independently represents a phenyl group, a benzyl group, a naphthyl group (the aryl portion of these groups may have one or more substituents, which may be the same or different in kind, selected from the class consisting of a $C_{1-4}$ alkyl group, a $C_{1-4}$ alkoxy group, a halogen atom and a nitro group), a hydrogen atom, or a $C_{1-4}$ alkyl group]}, or salt thereof, or a hydrate of the compound or salt;

the above-described compound, wherein the compound represented by the formula (II-AD) has a configuration of the following formula:

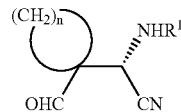

(wherein, n and $R^1$ have the same meanings as described above), or salt thereof, or the hydrate of the compound or salt;

a compound represented by formula (III):

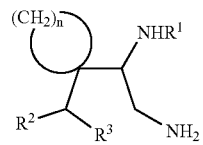

III

{wherein, n stands for an integer of from 2 to 5,
R$^1$ represents a hydrogen atom or a group represented by formula:

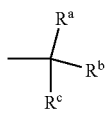

[wherein, R$^a$, R$^b$ and R$^c$ each independently represents a phenyl group, a benzyl group, a naphthyl group (the aryl portion of these groups may have one or more substituents, which may be the same or different in kind, selected from the class consisting of a C$_{1-4}$ alkyl group, a C$_{1-4}$ alkoxy group, a halogen atom and a nitro group), a hydrogen atom, or a C$_{1-4}$ alkyl group], and
R$^2$ and R$^3$ each independently represents a C$_{1-4}$ alkoxy group or may be integrated together to form a group represented by the formula:

(wherein, m stands for an integer of from 1 to 4)}, or salt thereof, or a hydrate of the compound or salt;
the above-described compound, wherein the compound represented by formula (III) has a configuration of the following formula:

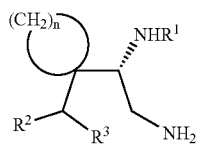

(wherein, n, R$^1$, R$^2$ and R$^3$ have the same meanings as described above), or salt thereof, or the hydrate of the compound or salt;
the above-described compound, wherein R$^2$ and R$^3$ each represents a C$_{1-4}$ alkoxy group, or salt thereof;
the above-described compound, wherein R$^2$ and R$^3$ each represents an ethoxy group, or salt thereof;
a compound represented by formula (III-ALD):

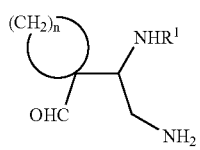

III-ALD

{wherein, n stands for an integer of from 2 to 5, and
R$^1$ represents a hydrogen atom or a group represented by formula:

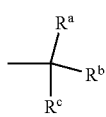

(wherein, R$^a$, R$^b$ and R$^c$ each independently represents a phenyl group, a benzyl group, a naphthyl group (the aryl portion of these groups may have one or more substituents, which may be the same or different in kind, selected from the class consisting of a C$_{1-4}$ alkyl group, a C$_{1-4}$ alkoxy group, a halogen atom and a nitro group), a hydrogen atom, or a C$_{1-4}$ alkyl group]}, or salt thereof, or a hydrate of the compound or salt;
the above-described compound, wherein the compound represented by the formula (III-ALD) has a configuration of the following formula:

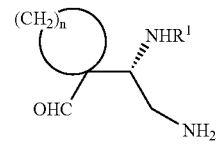

(wherein, n and R$^1$ have the same meanings as described above), or salt thereof, or a hydrate of the compound or salt;
a compound represented by formula (IV):

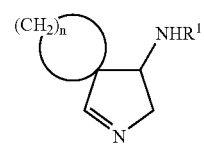

IV

{wherein, n stands for an integer of from 2 to 5, and
R$^1$ represents a hydrogen atom or a group represented by formula:

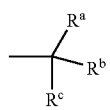

[wherein, R$^a$, R$^b$ and R$^c$ each independently represents a phenyl group, a benzyl group, a naphthyl group (the aryl portion of these groups may have one or more substituents, which may be the same or different in kind, selected from the class consisting of a C$_{1-4}$ alkyl group, a C$_{1-4}$ alkoxy group, a halogen atom and a nitro group), a hydrogen atom, or a C$_{1-4}$ alkyl group]}, or salt thereof, or a hydrate of the compound or salt;
the above-described compound, wherein the compound represented by the formula (IV) has a configuration of the following formula:

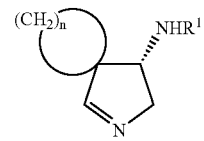

(wherein, n and R$^1$ have the same meanings as described above), or salt thereof, or a hydrate of the compound or salt;
a compound represented by formula (XI):

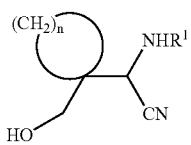

{wherein, n stands for an integer of from 2 to 5, and
R¹ represents a hydrogen atom or a group represented by formula:

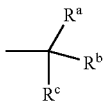

[wherein, R$^a$, R$^b$ and R$^c$ each independently represents a phenyl group, a benzyl group, a naphthyl group (the aryl portion of these groups may have one or more substituents, which may be the same or different in kind, selected from the class consisting of a $C_{1-4}$ alkyl group, a $C_{1-4}$ alkoxy group, a halogen atom and a nitro group), a hydrogen atom, or a $C_{1-4}$ alkyl group]}, or salt thereof, or a hydrate of the compound or salt;

the above-described compound, wherein n stands for 2, or salt thereof, or the hydrate of the compound or salt;

the above-described compound, wherein R¹ represents a group represented by formula:

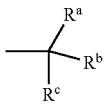

[wherein, R$^a$, R$^b$ and R$^c$ each independently represents a phenyl group, a benzyl group, a naphthyl group (the aryl portion of these groups may have one or more substituents, which may be the same or different in kind, selected from the class consisting of a $C_{1-4}$ alkyl group, a $C_{1-4}$ alkoxy group, a halogen atom and a nitro group), a hydrogen atom, or a $C_{1-4}$ alkyl group], or salt thereof, or the hydrate of the compound or salt;

the above-described compound, wherein R$^a$, R$^b$ and R$^c$ represent different groups each other, or salt thereof, or the hydrate of the compound or salt;

the above-described compound, wherein R$^a$, R$^b$ and R$^c$ are each a substituent selected from the class consisting of a hydrogen atom, a methyl group, an ethyl group, a phenyl group, a 4-methylphenyl group, a 4-methoxyphenyl group, a 4-chlorophenyl group, a 4-nitrophenyl group, a 2,4-dichlorophenyl group, a 2,4-dinitrophenyl group, a 3,5-dichlorophenyl group, a 3,5-dinitrophenyl group and a naphthyl group, or salt thereof, or the hydrate of the compound or salt;

the above-described compound, wherein substituent R¹ is a group selected from the class consisting of (R)-1-phenylethyl, (S)-1-phenylethyl, (R)-1-phenylpropyl, (S)-1-phenylpropyl, (R)-1-phenyl-2-(p-tolyl)ethyl, (S)-1-phenyl-2-(p-tolyl)ethyl, (R)-1-(1-naphthyl)ethyl, (S)-1-(1-naphthyl)ethyl, (R)-1-(4-methoxyphenyl)ethyl, (S)-1-(4-methoxyphenyl)ethyl, (R)-1-(4-chlorophenyl)ethyl, (S)-1-(4-chlorophenyl)ethyl, (R)-1-(4-nitrophenyl)ethyl, (S)-1-(4-nitrophenyl)ethyl, (R)-1-(2,4-dichlorophenyl)ethyl, (S)-1-(2,4-dichlorophenyl)ethyl, (R)-1-(2,4-dinitrophenyl)ethyl, (S)-1-(2,4-dinitrophenyl)ethyl, (R)-1-(3,5-dichlorophenyl)ethyl, (S)-1-(3,5-dichlorophenyl)ethyl, (R)-1-(3,5-dinitrophenyl)ethyl, and (S)-1-(3,5-dinitrophenyl)ethyl groups, or salt thereof, or the hydrate of the compound or salt;

the above-described compound, wherein the substituent R¹ is an (R)-1-phenylethyl or (S)-1-phenylethyl group, or salt thereof, or the hydrate of the compound or salt; and the like.

MODE FOR CARRYING OUT THE INVENTION

The present invention will next be described more specifically. In the specification of the present application, the term "optically single" or "stereochemically single" means that the compound has a structure permitting existence of plurality of isomers, but it is a compound composed of any one of these isomers. It embraces not only a compound utterly free of another isomer but also a compound containing it in an amount regarded as chemically pure. In other words, it may contain another isomer in an amount within an extent not influencing on the physical constant or physiological activity of the compound.

Preparation processes according to the invention of the present application will hereinafter be described.

Described first is a preparation process of the compound of the formula (II). The compound of the formula (II) can be prepared either one of two processes, that is, Process A and Process B.

Process A

A compound represented by formula (I):

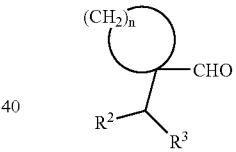

is available by selective acetalization of one of the aldehyde groups of a compound represented by the following formula:

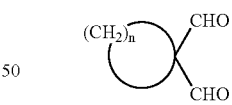

The dialdehyde compound of the above-described formula wherein n stands for 2 is a known compound (JP-A-8-133997). The selective acetalization of the present invention may be effected by reacting the dialdehyde compound with an acetalization agent in the presence of a catalyst and if desired, in the presence of an additive. As the acetalization agent, an alkyl orthoformate or alcohol is usable, while as the additive, a dehydrating agent such as anhydride of an inorganic salt is usable or an alkyl orthoformate itself may be added as the additive to accelerate the reaction.

The catalyst to be used in the present reaction may be an acid. Either an organic acid or inorganic acid is usable. Examples of the inorganic acid include hydrochloric acid and sulfuric acid. Lewis acids such as aluminum chloride, zinc chloride and boron trifluoride are also usable. Example of the organic acid include carboxylic acids which may have a substituent and sulfonic acids which may have a substituent. As the carboxylic acids which may have a substituent, trifluoroacetic acid and the like are preferred, while as the sulfonic acids which may have a substituent, aromatic sulfonic acids which may have a substituent and aliphatic sulfonic acids which may have a substituent are usable. Examples of the aromatic sulfonic acid compounds which may have a substituent include benzenesulfonic acid and paratoluenesulfonic acid, while those of the aliphatic sulfonic acid compounds which may have a substituent include methanesulfonic acid, trifluoromethanesulfonic acid and camphor sulfonic acid. As the acid catalyst, sulfonic acid compounds are preferred. It may be added in a catalytic amount.

No particular limitation is imposed on the solvent to be used in the present reaction insofar as it has no adverse effect on the reaction. Examples include aromatic hydrocarbons (benzene, toluene, chlorobenzene, etc.), aliphatic hydrocarbons (pentane, hexane, cyclohexane, etc.), ethers (diethyl ether, diisopropyl ether, tetrahydrofuran, dioxane, 1,2-dimethoxyethane, etc.), amides (N,N-dimethylformamide, N,N-dimethylacetamide, N-methyl-2-pyrrolidone, etc.), halogenated hydrocarbons (dichloromethane, chloroform, dichloroethane, etc.), esters (ethyl acetate, etc.), acetonitrile, and the like. The reaction can be effected also in ketones (acetone, methyl ethyl ketone, etc.).

The present reaction may be effected at a temperature ranging from about −50 to 100° C., preferably 0 to 60° C.

The selective acetalization is carried out as described below. The method can be classified roughly into two types.

One is to react a dialdehyde compound with an alkyl orthoformate in the presence of an acid catalyst. In this reaction, the alkyl orthoformate acts as an acetalization agent. The alkyl orthoformate having a structure corresponding to the substituents $R^2$ and $R^3$ of the compound represented by the formula (I) may be used. Described specifically, as the alkyl orthoformate, methyl orthoformate may be selected when $R^2$ and $R^3$ each represents a methoxy group, while ethyl orthoformate may be selected when they are each an ethoxy group. The alkyl orthoformate may be added in an amount of from 1 equivalent to 2 equivalents relative to the dialdehyde compound, with an amount of from 1 to 1.5 equivalents being preferred. This process enables preparation of the target compound (I) (monoacetal compound) at an excellent yield and selectivity when effected at a temperature range of from 0 to 30° C. For example, ethyl orthoformate (1.1 equivalents) was used for the reaction with 1,1-cyclopropanedicarboaldehyde in toluene by using paratoluenesulfonic acid as a catalyst, monoacetalization (meaning acetalization of one of the aldehyde groups of the dialdehyde compound) proceeded at a selectivity of 95% or greater.

In the next place, a process to prepare an acetal compound from the dialdehyde compound and an alcohol in the presence of an acid catalyst will be described. Excellent yield and selectivity are attained when this method is conducted in the presence of an additive.

First, a method to add a dehydrating agent as the additive will be described. The dehydrating agent is effective for removing water generated upon acetalization, thereby shifting the equilibrium toward the formation of acetal.

Any dehydrating agent is usable insofar as it is inert to the reaction. For example, an anhydride of an inorganic acid is usable and, in particular, that having a high dehydrating capacity is preferred. Specific examples include anhydrous magnesium sulfate. Anhydrous sodium sulfate or molecular sieves are also usable. Although it may be added within a range of from an amount sufficient to trap the resulting water to a large excess, use of an equimolar amount to the dialdehyde compound is convenient.

Similar to the orthoformate, an alcohol having a structure corresponding to the substituent $R^2$ and $R^3$ of the compound represented by the formula (I) may be used. For example, as the alcohol, methanol may be selected when $R^2$ and $R^3$ are each a methoxy group and ethanol may be selected when they are each an ethoxy group. The alcohol may be used in an amount ranging from two equivalents to a large excess relative to the dialdehyde compound (the alcohol can be made to serve also as a solvent).

For example, the reaction was effected using ethanol, which also serves as a solvent, in the presence of anhydrous magnesium sulfate (equimolar amount) and a catalytic amount of paratoluenesulfonic acid, whereby the target compound (I) was obtained at a selectivity of about 9:1.

In the process for preparing an acetal compound from the dialdehyde compound and alcohol, use of an alkyl orthoformate as an additive can bring about excellent results. In this case, the alkyl orthoformate is considered to act as a reaction accelerator. The alcohol may be added in a stoichiometric amount (or greater), while the alkyl orthoformate may be added in a catalytic amount. For example, it may be added in an amount of from about 0.1 to 0.2 equivalent relative to the dialdehyde compound.

The above-described preparation process of the compound (I) is suited for the preparation of the compound (I) having the same alkoxy group as the substituents $R^2$ and $R^3$. A compound different in the alkoxy group between the substituents $R^2$ and $R^3$ or having an alkylenedioxy group can be obtained by preparing an acetal compound having, as $R^2$ and $R^3$, the same alkoxy group, followed by transacetalization. Alternatively, such a compound can be obtained by preparing a hemiacetal in advance and then reacting it with another acetalization agent.

Step from Compound (I) to Compound (II)

A preparation process of a compound represented by formula (II):

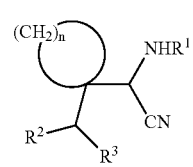

II will next be described. The compound is available by the so-called Strecker reaction, that is, by reacting a compound of the formula (I) with a cyanation agent in the presence of a compound represented by formula (VI):

    VI ($R^1$ may be a substituent as described above) or salt thereof.

Acid addition salts are usable as the salt of the compound represented by the formula (VI). Examples include inorganic acid salts such as hydrochlorides, hydrobromides and nitrates. When these salts are used, it is necessary to separately add a base in an amount sufficient to convert them into the corresponding free base.

As the compound of the formula (VI), preferred is that having an asymmetric carbon, more preferably a compound having either one of two optical isomers, that is, optically single compound.

Examples of the compound represented by the formula (VI) include (R)- or (S)-1-phenylethylamine, (R)- or (S)-1-phenylpropylamine, (R)- or (S)-1-phenyl-2-(p-tolyl)ethylamine, (R)- or (S)-1-(1-naphthyl)ethylamine, (R)- or (S)-1-(4-methoxyphenyl)ethylamine, (R)- or (S)-1-(4-chlorophenyl)ethylamine, (R)- or (S)-1-(4-nitrophenyl)ethylamine, (R)- or (S)-1-(2,4-dichlorophenyl)ethylamine, (R)- or (S)-1-(2,4-dinitrophenyl)ethylamine, (R)- or (S)-1-(3,5-dichlorophenyl)ethylamine, and (R)- or (S)-1-(3,5-dinitrophenyl)ethylamine.

The cyanation agent to be used in the present step may be hydrogen cyanide or a cyan compound.

When hydrogen cyanide is employed for the reaction, it may be introduced in the reaction system as a gas generated outside the system or the gas may be generated directly in the reaction system. When it is generated in the reaction system, salt exchange reaction in water between an alkali cyanide such as potassium cyanide, sodium cyanide or lithium cyanide and an acid substance typified by hydrochloric acid can be utilized. The gas may be generated by adding a reducing agent such as sodium bisulfite to the alkali cyanide.

Various cyan compounds may be used instead of hydrogen cyanide for the reaction. Examples of such a cyan compound include cyanhydrin compounds such as acetone cyanhydrin and cyclohexanone cyanhydrin, organic cyan compounds such as trimethylsilyl cyanide and diethylphosphoryl cyanide, and organometal cyan compounds such as diethylaluminum cyanide and tributyltin cyanide. Since only the addition to the reaction mixture causes progress of the reaction, these cyan compounds are convenient and, in addition they have high safety, they are therefore advantageous in this step.

In the present reaction, any solvent is usable insofar as it has no adverse effect on the reaction. Examples include alcohols such as methanol, ethanol and propanol, ethers such as tetrahydrofuran and dioxane, ketones such as acetone, nitrogenous solvents such as acetonitrile, aromatic hydrocarbons such as toluene, aliphatic hydrocarbons such as hexane and cyclohexane, esters such as ethyl acetate, amides such as dimethylformamide and dimethylacetamide, and halogenated hydrocarbons such as dichloromethane and chloroform. These solvents may be used as a solvent mixture, or if necessary a hydrous solvent. Use of an alcohol or hydrous alcohol as the solvent is preferred.

When the present step is effected using hydrogen cyanide, it is preferred in consideration of convenience to mix, in advance, the compound represented by the formula (I), the compound represented by the formula (VI), a compound serving as a source for generating hydrogen cyanide (such as the above-described alkali cyanide, organic cyan compound or organometal cyan compound) in a solvent and then, add a hydrogen cyan generating agent to the resulting solution.

When the present step is effected using a cyan compound such as acetone cyanhydrin, addition of a hydrogen cyanide generating agent is not necessary, which makes the step more convenient and preferable.

The present step, in any case, may be conducted at a temperature ranging from about −20° C. to 100° C., preferably from about room temperature to the boiling point of the solvent.

When the present reaction is conducted with an optically single amine, the product is a mixture of two diastereomers and one of the diastereomer is preferentially formed to the other one. Diastereoselective progress is the characteristic of the present reaction. For example, when (S)-1-phenylethylamine was used as the amine, the product was a mixture of (2S)-2-[1-(diethoxymethyl)cyclopropyl]-2-{[(1S)-1-phenylethyl]amino}acetonitrile and a diastereomer thereof, that is, (2R)-2-[1-(diethoxymethyl)cyclopropyl]-2-{[(1S)-1-phenylethyl]amino}acetonitrile. Their formation ratio was 2:1 (accordingly, when (R)-1-phenylethylamine is employed, the product is a mixture of (2S)-2-[1-(diethoxymethyl)cyclopropyl]-2-{[(1R)-1-phenylethyl]amino}acetonitrile and a diastereomer thereof, that is, (2R)-2-[1-(diethoxymethyl)cyclopropyl]-2-{[(1R)-1-phenylethyl]amino}acetonitrile, but their formation ratio is presumed to be about 1:2).

The two diastereomers thus obtained can be separated in a conventional manner. For example, crystallization (when the compound takes the form of crystals) and also chromatography on a silica gel column, thin-layer chromatography and high-performance liquid chromatography may be employed for separation.

Of the optically active substances thus obtained by separation, an unnecessary isomer can be converted easily into a mixture of diastereomers containing a necessary isomer by treating it in a polar solvent, thereby causing epimerization, in other words, by converting a configuration of the carbon atom to which an amino group and cyano group are bonded. From the mixture, a compound having the target configuration can be separated.

Any polar solvent is usable insofar as it has no adverse effect on the reaction. Protonic solvents are preferred. Specific examples include alcohols such as methanol, ethanol, propanol and isopropanol. Alternatively, a solvent mixture of such a protonic solvent with another solvent may be used. Examples of the another solvent include ethers such as tetrahydrofuran, ketones such as acetone and nitrogenous solvents such as acetonitrile.

The epimerization may be effected by heating. Heating of (2R)-2-[1-(diethoxymethyl)cyclopropyl]-2-{[(1S)-1-naphthylethyl]amino}acetonitrile in ethanol yielded a 2.9:1 mixture of (2S)-2-[1-(diethoxymethyl)cyclopropyl]-2-{[(1S)-1-naphthylethyl]amino}acetonitrile and (2R)-2-[1-(diethoxymethyl)cyclopropyl]-2-{[(1S)-1-naphthylethyl]amino}acetonitrile. Thus, conversion to an optically active substance having the target configuration can be conducted easily.

Based on the fact that when one diastereomer is apt to precipitate as a crystal (solid), the other diastereomer is converted into the one diastereomer, the inventors of the present application considered that conversion, and crystallization and isolation of diastereomer can be conducted as a series of steps. In other words, they considered that crystallization and conversion of a diastereomer can be conducted successively by, after completion of the Strecker reaction, adding water or the like to the reaction mixture in order to decrease the solubility in the solvent and then heating. As a result, they succeeded in preparation of the target diastereomer in a high yield by the above-described method. Described specifically, by decreasing the solubility of the reaction mixture in the solvent, precipitation of one diastereomer is accelerated. The other diastereomer having a high solubility exists in the dissolved form in the reaction mixture, and heating accelerates the conversion of it to the one diastereomer. The resulting diastereomer precipitates because of a small solubility. By this precipitation, further conversion into the one diastereomer proceeds.

To carry out the above-described method, it is necessary to add to the reaction mixture, after completion of the Strecker reaction, a substance capable of decreasing the solubility of the solvent used in the reaction. No particular limitation is imposed on such a substance insofar as it is miscible with the reaction solvent and has no adverse effect on the product. For a solvent miscible with water such as alcohol, dioxane, tetrahydrofuran, acetonitrile or acetone, water can be added. For a solvent immiscible with water, a hydrocarbon such as hexane or benzene can be added. Such a substance to decrease the solubility of the solvent may be added within an extent not causing precipitation of an unnecessary diastereomer.

Heating in this step may be conducted at a temperature within an extent not causing re-dissolution of precipitated crystals, but lower temperatures are preferred. For example, heating at about 30 to 60° C. is preferred, with about 40 to 50° C. being more preferred.

The compound (II) having, as a substituent $R^1$, an alkoxycarbonyl group, aralkyloxycarbonyl group, or an aliphatic or aromatic acyl group is easily available by conversion of the compound of the formula (II) having, as $R^1$, a hydrogen atom in accordance with ordinarily employed substitution reaction.

Process B

Step from Compound (X) to Compound (XI)

A compound of the formula (XI) is available by conducting the so-called Strecker reaction, more specifically, by reacting a compound of the formula (X) with a cyanation agent in the presence of a compound represented by formula (VI):

$$H_2N-R^1 \qquad\qquad VI$$

The compound of the formula (X) wherein n stands for 2 can be obtained by the process as shown in Referential Example 2 or Referential Example 3 (Japanese Patent Application No. 2001-044405).

In the present reaction, hydrogen cyanide or a cyan compound may be used as the cyanation agent.

When hydrogen cyanide is employed for the reaction, it may be introduced as a hydrogen cyanide gas generated outside the reaction system or it may be generated directly in the reaction system. When it is generated directly in the reaction system, salt exchange reaction in water between an alkali metal cyanide such as potassium cyanide, sodium cyanide or lithium cyanide and an acid substance can be utilized. The gas can be generated by adding a reducing agent such as sodium bisulfite to the alkali metal cyanide.

When a cyan compound is employed for the reaction, examples of it include cyanhydrin compounds such as acetone cyanhydrin, organic cyan compounds such as trimethylsilyl cyanide and organometal cyan compounds such as diethylaluminum cyanide.

Examples of the compound represented by the formula (VI) include (R)- or (S)-1-phenylethylamine, (R)- or (S)-1-phenylpropylamine, (R)- or (S)-1-phenyl-2-(p-tolyl)ethylamine, (R)- or (S)-1-(1-naphthyl)ethylamine, (R)- or (S)-1-(4-methoxyphenyl)ethylamine, (R)- or (S)-1-(4-chlorophenyl)ethylamine, (R)- or (S)-1-(4-nitrophenyl)ethylamine, (R)- or (S)-1-(2,4-dichlorophenyl)ethylamine, (R)- or (S)-1-(2,4-dinitrophenyl)ethylamine, (R)- or (S)-1-(3,5-dichlorophenyl)ethylamine, and (R)- or (S)-1-(3,5-dinitrophenyl)ethylamine.

In the present reaction, any solvent is usable insofar as it has no adverse effect on the reaction. Examples include alcohols such as methanol, ethanol and propanol, ethers such as diethyl ether, tetrahydrofuran and dioxane, ketones such as acetone, nitrogenous solvents such as acetonitrile, aromatic hydrocarbons such as benzene and toluene, aliphatic hydrocarbons such as hexane and cyclohexane, esters such as ethyl acetate, amides such as dimethylformamide and dimethylacetamide, and halogenated hydrocarbons such as dichloromethane and chloroform. These solvents may be used as a solvent mixture, or if necessary a hydrous solvent. Of these, a hydrous alcohol is preferred.

The present reaction, in any case, may be effected at a temperature ranging from about −20° C. to 100° C., preferably from about room temperature to the boiling point of the solvent.

Step from Compound (XI) to Compound (II-ALD)

A compound represented by the formula (II-ALD) is available by acting an oxidant on the compound represented by the formula (XI) and then terminating the oxidation of a primary hydroxyl group at the stage of an aldehyde.

Any oxidant is usable in the present reaction insofar as it is capable of terminating the oxidation of a primary hydroxyl group at the stage of aldehyde. Examples include a Collins reagent, pyridinium chlorochromate (PCC), pyridinium dichromate (PDC), Dess-Martin, and Periodinane. Of these, pyridinium chlorochromate is preferred. Alternatively, Swern oxidation or the like oxidation reaction by which a primary hydroxyl group is converted into an aldehyde can be adopted.

In the present reaction, any solvent is usable insofar as it has no adverse effect on the reaction. Examples include ethers such as diethyl ether, tetrahydrofuran and dioxane, ketones such as acetone, nitrogenous solvents such as acetonitrile, aromatic hydrocarbons such as benzene and toluene, aliphatic hydrocarbons such as hexane and cyclohexane, esters such as ethyl acetate, amides such as dimethylformamide and dimethylacetamide, and halogenated hydrocarbons such as dichloromethane and chloroform. Of these, halogenated hydrocarbons are preferred, with dichloromethane being particularly preferred.

The present reaction may be effected at a temperature ranging from about −78° C. to the boiling point of the solvent, which however depends on the conditions of the oxidation reaction.

Step from Compound (II-ALD) to Compound (II)

A compound represented by the formula (II) may be obtained by acetalizing the compound represented by the formula (II-ALD) by acting thereon an alkyl orthoformate in the presence of an acid catalyst, while adding an alcohol if desired.

As the alkyl orthoformate, that having, as the alkyl portion thereof, a structure corresponding to the substituents $R^2$ and $R^3$ of the compound represented by the formula (II) may be used. For example, the alkyl portion of the alkyl orthoformate is a methyl group when $R^2$ and $R^3$ are each a methoxy group, while the alkyl portion is an ethyl group when they are each an ethoxy group. If an alcohol is added, that similar to the alkyl portion of the alkyl orthoformate may be used, for example, methyl alcohol for methyl orthoformate and ethyl alcohol for ethyl orthoformate.

As the acid catalyst used in the present reaction, either an organic acid or inorganic acid is usable. Example of the organic acid include carboxylic acids such as acetic acid and trifluoroacetic acid, and sulfonic acids such as methanesulfonic acid, p-toluenesulfonic acid and trifluoromethanesulfonic acid. Examples of the inorganic acid include hydrochloric acid and sulfuric acid. Lewis acids such as titanium tetrachloride and boron trifluoride are also usable. Of these, p-toluenesulfonic acid is desired. The acid may be used in a catalytic amount and may range from ¹/₁₀ to ¹/₁₀₀ mol relative to Compound (II-ALD).

Any solvent is usable in the present reaction insofar as it has no adverse effect on the reaction. Examples include ethers such as diethyl ether, tetrahydrofuran and dioxane, ketones such as acetone, nitrogenous solvents such as acetonitrile, aromatic hydrocarbons such as benzene and toluene, aliphatic hydrocarbons such as hexane and cyclohexane, esters such as ethyl acetate, amides such as dimethylformamide and dimethylacetamide, and halogenated hydrocarbons such as dichloromethane and chloroform.

The present reaction, in any case, may be effected at a temperature ranging from about room temperature to 100° C.

The above-described preparation process of the compound (II) is suited for the preparation of the compound (II) having the same alkoxy group as the substituents $R^2$ and $R^3$. A compound different in the alkoxy group between the substituents $R^2$ and $R^3$ or having an alkylenedioxy group can be obtained by preparing an acetal compound having, as $R^2$ and $R^3$, the same alkoxy group, followed by transacetalization. Alternatively, such a compound can be obtained by preparing a hemiacetal in advance and then reacting it with another acetalization agent.

Step from Compound (II) to Compound (III)

A description will next be made of a process for preparing a compound represented by formula (III):

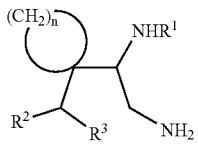

III from the compound represented by the formula (II).

The target compound can be prepared by reducing the cyano group of the compound represented by the formula (II). This reduction may be conducted by the catalytic hydrogenation reaction in the presence of an acid catalyst in a hydrogen gas atmosphere. Any reaction can be employed insofar as it is inert to $R^1$ and is capable of reducing a cyano group into an aminomethyl group. Examples of the catalyst usable for the catalytic hydrogenation reaction include palladium-carbon, palladium hydroxide, Raney-nickel and Raney-cobalt. Of these, Raney-nickel and Raney-cobalt are particularly preferred.

Any solvent is usable in the present reaction insofar as it has not adverse effect on the reaction. Preferred examples include alcohols such as methanol, ethanol, propanol and isopropanol and ethers such as 1,4-dioxane. Such a solvent may have, dissolved therein, an alkali component, such as an alkali hydroxide, e.g., sodium hydroxide or potassium hydroxide, or ammonia. In this case, the solvent may be mixed with water. An ammonia-containing solvent may be prepared by dissolving an ammonia gas or mixing aqueous ammonia in the solvent.

The catalytic hydrogenation reaction may be effected at a temperature ranging from 0° C. to 50° C., preferably from 5° C. to about room temperature. The pressure of a hydrogen gas upon catalytic hydrogenation may range from normal pressure to 100 atm. When the catalytic hydrogenation is conducted at about room temperature, ring-closure reaction by continuously heating to from about 50° C. to 180° C. is required.

Alternatively, the compound of the formula (III) is available by hydride reduction of the compound of the formula (II). Upon hydride reduction, any one of lithium aluminum hydride, diisobutylaluminum hydride, sodium bis(2-methoxyethoxy)aluminum hydride, sodium cyanoborohydride and sodium borohydride may be used in accordance with the ordinarily employed method.

Step from Compound (III) to Compound (IV)

A preparation process of a compound represented by formula (IV):

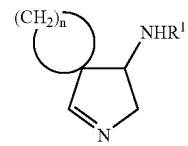

IV from the compound represented by the formula (III) will next be described.

The target compound may be prepared by removal of acetal from the compound of the formula (III), thereby introducing it into the corresponding aldehyde compound,

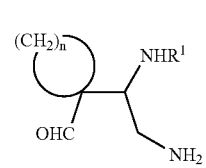

III-ALD and then subjecting the aldehyde compound to ring-closure. Acetal can be removed by acting water on the compound of the formula (III) in the presence of an acid. Either an organic acid or an inorganic acid is usable in the reaction, but use of hydrochloric acid, sulfuric acid, paratoluenesulfonic acid, acetic acid or the like is preferred.

Acetal is removed in the presence of an ordinarily employed solvent. No particular limitation is imposed on the solvent insofar as it has not adverse effect on the reaction. As the solvent, water or a solvent miscible with water is preferred. Examples of the solvent miscible with water include alcohols such as methanol, ethanol, propanol and isopropanol, ethers such as tetrahydrofuran and dioxane, ketones such as acetone and nitrogenous solvents such as acetonitrile.

The present reaction may be conducted at a temperature ranging from −50° C. to the boiling point of the solvent, with a temperature range of from 0° C. to about room temperature is preferred.

The ring closure of the compound from which acetal has been removed may be conducted under neutral or basic conditions. The ring closure reaction proceeds by making the reaction mixture, which has remained after acetal removal, neutral or basic. Alternatively, the ring closure reaction may be carried out in the presence of a dehydrating agent after neutralization and then, extraction with a solvent for isolation. There is no particular limitation imposed on the solvent usable in the ring-closure step insofar as it has no adverse effect on the reaction. Examples include aromatic hydrocarbons, aliphatic hydrocarbons, ethers, amides, halogenated hydrocarbons, and in addition, acetonitrile, acetone and ethyl acetate. The ring closure may be conducted at a temperature ranging from −50° C. to the boiling point of the solvent, with a temperature range of from 0° C. to about room temperature being preferred.

Step from Compound (IV) to Compound (VII)

A preparation process of a compound represented by formula (VII):

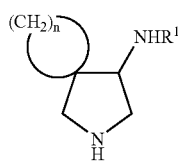

from the compound represented by the formula (IV) will next be described.

The compound may be prepared by catalytic hydrogenation or hydride reduction of the compound represented by the formula (IV).

Examples of the catalyst usable upon the catalytic hydrogenation reaction include palladium-carbon, palladium hydroxide, Raney-nickel and Raney-cobalt. Of these, Raney-nickel and Raney-cobalt are particularly preferred. Examples of the hydride reducing agent include metal aluminum hydride compounds and metal borohydride compounds, such as lithium aluminum hydride, diisobutylaluminum hydride, sodium bis(2-methoxyethoxy)aluminum hydride, sodium cyanoborohydride and sodium borohydride. Of these, metal borohydride compounds are preferred, with sodium cyanoborohydride being particularly preferred.

Any solvent is usable in the present reaction insofar as it has no adverse effect on the reaction. Preferred examples include alcohols such as methanol, ethanol, propanol, and isopropanol and ethers such as tetrahydrofuran. The present reaction may also be effected adding water to the above-described solvent.

The present reaction may be conducted at a temperature ranging from −50° C. to 100° C., preferably from 0° C. to room temperature. Upon catalytic hydrogenation, the pressure of a hydrogen gas may range from 1 to 100 atm.

Step from Compound (VII) to Compound (VIII)

A compound represented by formula (VIII):

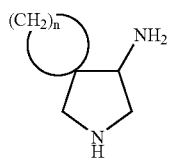

can be prepared by converting $R^1$ (except hydrogen) of the compound represented by the formula (VII) into a hydrogen atom in an ordinarily employed manner such as catalytic hydrogenolysis.

When catalytic hydrogenolysis reaction is used, palladium-carbon, palladium hydroxide, Raney-nickel or the like is usable as the catalyst, but palladium-carbon and palladium hydroxide are particularly preferred. As the solvent, any one free of adverse effect on the reaction is usable. Preferred examples include alcohols such as methanol, ethanol, propanol and isopropanol and ethers such as tetrahydrofuran. The present reaction may be effected adding water to the above-described solvent. In some cases, an acid such as acetic acid or hydrochloric acid added upon reaction.

The present reaction may be conducted at a temperature ranging from 0° C. to 100° C., preferably from 5° C. to 50° C. In the present reaction, the pressure of a hydrogen gas may range from 1 to 100 atm, preferably from 1 to 50 atm.

The compound of the formula (VIII) obtained by the preparation process of the present invention can be introduced into an excellent antibacterial agent by the process as described in JP-A-2-231475 and JP-A-3-95176.

Step from Compound (VII) to Compound (XII)

A preparation process of a compound represented by formula (XII):

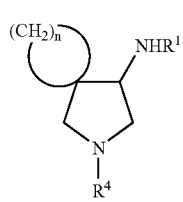

from the compound represented by the formula (VII) will next be described. The target compound is available by subjecting the amino group constituting the pyrrolidine ring of the compound represented by the formula (VII) to acylation, alkoxycarbonylation, aralkylation or the like. By such a reaction, a substituent may be introduced to the amino group to protect it. It is preferred that $R^4$ and $R^1$ are different groups, particularly, groups which can be removed under different conditions.

As the acylating agent used for acylation, acid anhydrides and acid halides are usable. Examples of the acid anhydride include acetic anhydride, trifluoroacetic anhydride, phenylacetic anhydride, propionic anhydride and benzoic anhydride. Examples of the acid halide include acetyl chloride, acetyl bromide, propionyl chloride and benzoyl chloride. Examples of the alkoxycarbonylating agent include di-tert-butyl dicarbonate, those of the aralkyloxycarbonylating agent include benzyloxycarbonyl chloride and those of the aralkylating agent include benzyl chloride and benzyl bromide.

Such a reaction causing agent to be added to introduce a protecting group may be added in an amount of one equivalent to an excess amount, preferably from 1 to 2 equivalents, relative to the compound (VII). Use of at least one equivalent of a tertiary amine or nitrogenous heterocyclic compound such as triethylamine or pyridine is preferred.

In the present reaction, any solvent is usable insofar as it has not adverse effect on the reaction. Examples include, as well as aromatic hydrocarbons, aliphatic hydrocarbons, ethers, amides, halogenated hydrocarbons, acetonitrile, acetone and ethyl acetate.

The present reaction may be conducted at a temperature ranging from about −50 to 100° C., preferably −20° C. to room temperature.

Step from Compound (XII) to Compound (XII-a)

A preparation process of a compound represented by formula (XII-a):

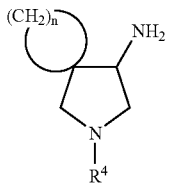

XII-a will next be described. This compound can be prepared by removing $R^1$ from the compound represented by the formula (XII) by catalytic hydrogenolysis or the like method.

When catalytic hydrogenolysis is used, palladium-carbon, palladium hydroxide, Raney-nickel or the like may be used as the catalyst, with palladium-carbon and palladium hydroxide being particularly preferred.

In the present reaction, any solvent is usable insofar as it has no adverse effect on the reaction. Preferred examples of the solvent include alcohols such as methanol, ethanol, propanol and isopropanol, and ethers such as tetrahydrofuran. The present reaction may be effected adding water to the above-described solvent. In some cases, an acid such as acetic acid or hydrochloric acid may be added upon reaction.

The present reaction may be conducted at a temperature ranging from 0° C. to 100° C., preferably from about the room temperature to the boiling point of the solvent. The present reaction is performed in a hydrogen gas atmosphere. Its pressure may range from 1 to 100 atm, preferably from 1 to 50 atm.

Step from Compound (XII-a) to Compound (XIII)

A preparation process of a compound represented by formula (XIII):

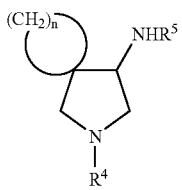

XIII will next be described. This compound is available by converting the primary amino group of the compound represented by the formula (XII-a) into the corresponding alkoxycarbonyl group, aralkyloxycarbonyl group, or aliphatic or aromatic acyl group by the ordinarily employed substitution reaction. In this reaction, it is preferred that $R^5$ and $R^4$ are different groups, particularly groups removable by different reaction conditions.

Examples of the alkoxycarbonylating agent include di-tert-butyl dicarbonate, those of the aralkyloxycarbonylating agent include benzyloxycarbonyl chloride, those of the acylating agent include acetic anhydride, trifluoroacetic anhydride, phenylacetic anhydride, propionic anhydride, benzoic anhydride, acetyl chloride, acetyl bromide, propionyl chloride and benzoyl chloride, and those of the aralkylating agent include benzyl chloride and benzyl bromide.

Such a reaction causing agent may be added in an amount of one equivalent to a large excess relative to the compound (XII-a). Use of a tertiary amine or nitrogenous heterocyclic compound such as triethylamine or pyridine is preferred.

In the present reaction, any solvent is usable insofar as it has not adverse effect on the reaction. Examples include alcohols such as methanol, ethanol, propanol and isopropanol, ethers such as tetrahydrofuran and dioxane, ketones such as acetone, nitrogenous solvents such as acetonitrile, aromatic hydrocarbons such as toluene, aliphatic hydrocarbons such as hexane, esters such as ethyl acetate, amides such as dimethylformamide and halogenated hydrocarbons such as dichloromethane. The above-described solvent is used as a hydrous solvent as needed.

The present reaction may be conducted at a temperature ranging from about −20 to 100° C., preferably from room temperature to the boiling point of the solvent.

Step from Compound (XIII) to Compound (XIV)

A preparation process of a compound represented by formula (XIV):

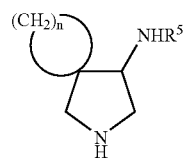

XIV will next be described. This compound is available by eliminating the protecting group of $R^4$ from the compound represented by the formula (XIII). Deprotection may be effected by hydrolysis when $R^4$ represents an acyl or alkoxycarbonyl group and by hydrogenolysis when it represents an aralkyl or aralkyloxycarbonyl group.

For deprotection, any solvent is usable insofar as it has not adverse effect on the reaction. Examples include alcohols such as methanol, ethanol, propanol and isopropanol, ethers such as tetrahydrofuran and dioxane, ketones such as acetone, nitrogenous solvents such as acetonitrile, aromatic hydrocarbons such as toluene, aliphatic hydrocarbons such as hexane, esters such as ethyl acetate, amides such as dimethylformamide, and halogenated hydrocarbons such as dichloromethane. These solvents may be used as a hydrous solvent as needed. Examples of the solvent miscible with water include alcohols such as methanol, ethanol, propanol and isopropanol, ethers such as tetrahydrofuran and dioxane, ketones such as acetone and nitrogenous solvents such as acetonitrile.

The reaction may be effected at a temperature ranging from −50° C. to 100° C., preferably from 0° C. to about the boiling point of the solvent.

The compound of the formula (XIV) obtained here can be introduced into an excellent antibacterial agent by the process as described in JP-A-2-231475 and JP-A-3-95176.

In the next place, the compounds of the invention according to the present application will be described.

A compound represented by formula (I):

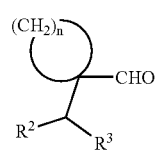

I has, as n, an integer of 2 to 5. The substituents $R^2$ and $R^3$ are each a $C_{1-4}$ alkoxy group or may be integrated together to form a methylenedioxy or polymethylenedioxy (alkylenedioxy) group. When $R^2$ and $R^3$ are each an alkoxy group, they may be the same or different, or may be either linear or branched. As $R^2$ and $R^3$, an alkoxy group such as methoxy, ethoxy or propoxy is preferred, with ethoxy group being most preferred. The compound having an ethoxy group as each of $R^2$ and $R^3$ is preferable from the viewpoint of convenient preparation.

The compound of the formula (I) is a compound having a structure in which one aldehyde group of a gem-dialdehyde compound has been selectively acetalized. One of the characteristics of the present invention resides in that selective acetalization of one aldehyde group of a dialdehyde compound can be attained and a monoacetal compound (which means a dialdehyde compound having one aldehyde group acetalized) is easily available.

A compound of the present invention represented by formula (II):

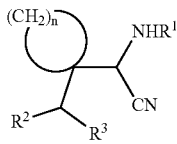

II will next be described and in the formula, n stands for an integer of 2 to 5. The substituent $R^1$ represents a hydrogen atom or a substituent represented by formula:

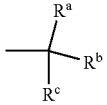

[wherein, $R^a$, $R^b$ and $R^c$ each independently represents a phenyl group, a benzyl group, a naphthyl group (the aryl portion of these groups may have one or more substituents, which may be the same or different in kind, selected from the class consisting of a $C_{1-4}$ alkyl group, a $C_{1-4}$ alkoxy group, a halogen atom and a nitro group), a hydrogen atom, or a $C_{1-4}$ alkyl group].

When $R^1$ represents a group of the following formula:

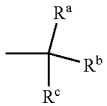

, no limitation is imposed on this group insofar as it undergoes no change even by the converting reaction of the cyano group of the compound of the formula (II) into an aminomethyl group and can protect an amino group.

With regards to the substituent $R^1$, the inventors of the present application have found that in order to obtain an isomer having a necessary configuration, the compound of the formula (II) is preferably a compound having a diastereomer-containing structure. The compound of the formula (II) has, as a carbon to which an amino group is bonded, an asymmetric carbon, meaning that the compound of the formula (II) has a diastereomer when the substituent $R^1$ contains an asymmetric carbon. The inventors of the present application have also found that upon preparation of the compound of the formula (II) which is a mixture of diastereomers, their yields are not uniform and one diastereomer is prepared preferentially to the other diastereomer. Which diastereomer is prepared preferentially can be controlled by the steric structure of the substituent $R^1$. In other words, it is possible to form a target diastereomer preferentially by changing the structure of the substituent $R^1$.

It has been revealed that in the above-described compound of the formula (II) which is a diastereomer mixture, a ratio of diastereomers varies by heating treatment. The inventors of the present application have also found that epimerization of one diastereomer occurs by heating treatment, which converts it into the other diastereomer, whereby a mixture containing the other diastereomer at an increased ratio is prepared. Also in this case, which diastereomer is preferentially formed can be controlled by conversion of the structure of the substituent $R^1$. By utilizing such a characteristic, a compound having an unnecessary configuration can be converted into a compound having a necessary configuration, whereby an isomer having a necessary configuration can be obtained efficiently. In the substituent $R^1$, therefore, $R^a$, $R^b$, and $R^c$ are different each other.

Specific examples of the $R^a$, $R^b$, and $R^c$ include a hydrogen atom, and methyl, ethyl, phenyl, 4-methylphenyl, 4-methoxyphenyl, 4-chlorophenyl, 4-nitrophenyl, 2,4-dichlorophenyl, 2,4-dinitrophenyl, 3,5-dichlorophenyl, 3,5-dinitrophenyl and naphthyl groups.

Specific examples of the $C_{1-4}$ alkoxy groups, halogen atoms and nitro group which are substituents on the aryl group include methyl group, methoxy group, nitro group and chlorine atom. One or more of the above-exemplified groups or atoms which may be the same or different in kind may be substituted on the aryl group.

Examples of the substituent $R^1$ in which $R^a$, $R^b$, and $R^c$ are different each other include (R)-1-phenylethyl, (S)-1-phenylethyl, (R)-1-phenylpropyl, (S)-1-phenylpropyl, (R)-1-phenyl-2-(p-tolyl)ethyl, (S)-1-phenyl-2-(p-tolyl)ethyl, (R)-1-(1-naphthyl)ethyl, (S)-1-(1-naphthyl)ethyl, (R)-1-(4-methoxyphenyl)ethyl, (S)-1-(4-methoxyphenyl)ethyl, (R)-1-(4-chlorophenyl)ethyl, (S)-1-(4-chlorophenyl)ethyl, (R)-1-(4-nitrophenyl)ethyl, (S)-1-(4-nitrophenyl)ethyl, (R)-1-(2,4-dichlorophenyl)ethyl, (S)-1-(2,4-dichlorophenyl)ethyl, (R)-1-(2,4-dinitrophenyl)ethyl, (S)-1-(2,4-dinitrophenyl) ethyl, (R)-1-(3,5-dichlorophenyl)ethyl, (S)-1-(3,5-dichlorophenyl)ethyl, (R)-1-(3,5-dinitrophenyl)ethyl, and (S)-1-(3,5-dinitrophenyl)ethyl groups. Of these, (R)-1-phenylethyl and (S)-1-phenylethyl groups are particularly preferred.

The substituent $R^1$ may be a protecting group of the amino group. In this case, no limitation is imposed on it insofar as it does not undergo a change even by the converting reaction of the cyano group of the compound (II) into an aminomethyl group. Examples of such an amino protecting group include alkoxycarbonyl groups which may have a substituent such as tert-butoxycarbonyl group and 2,2,2-trichloroethoxycarbonyl group, aralkyloxycarbonyl groups which may have a substituent such as benzyloxycarbonyl group, paramethoxybenzyloxycarbonyl group and paranitrobenzyloxycarbonyl group, aliphatic or aromatic acyl groups which may have a substituent such as acetyl group, methoxyacetyl group, trifluoroacetyl group, chloroacetyl group, pivaloyl group, formyl group, and benzoyl group, and aralkyl groups which may have a substituent such as benzyl group, paranitrobenzyl group, paramethoxybenzyl group and triphenylmethyl group.

Of these protecting groups, aralkyl groups are preferred from the viewpoint of preparation ease. Of the aralkyl groups, a benzyl group is more preferred. The phenyl group of the benzyl group may further have a substituent. It may have one or more substituents, which may be the same or different in kind, selected from the group consisting of $C_{1-4}$ alkyl groups, $C_{1-4}$ alkoxy groups, halogen atoms and nitro group. Specific example of the protecting group include, in addition to a benzyl group, 4-methoxybenzyl group, 4-chlorobenzyl group, 4-nitrobenzyl group, 2,4-dichlorobenzyl group, 2,4-dinitrobenzyl group, 3,5-dichlorobenzyl group and 3,5-dinitrobenzyl group.

Of the compounds represented by the formula (II), the compound whose amino group has a preferable configuration is a compound represented by the following formula:

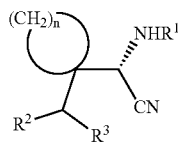

When the compound of the formula (II) is an acid addition salt, no particular limitation is imposed on the acid forming a salt insofar as it has no influence on the stability of the compound itself. As such an acid, either an inorganic acid or organic acid is usable. Examples of a salt with the inorganic acid include hydrochloride, hydrobromide, nitrate, phosphate and perchlorate, while those of a salt with the organic acid include salts with a carboxylic acid compound and those with a sulfonic acid compound. Examples of the carboxylate include acetate, fumarate and lactate, while those of the sulfonate include methanesulfonate, trifluoromethanesulfonate, benzenesulfonate and toluenesulfonate. These salts may take the form of a hydrate. This will equally apply to the formation of a salt with the below-described compounds.

The compound of the formula (II) is deacetalized by acid treatment or the like and then, becomes the corresponding aldehyde compound of the following formula:

II-ALD

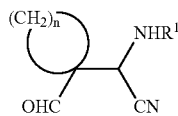

A compound of the present invention represented by formula (III):

III

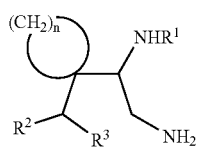

will next be described. In the formula, n, the substituents $R^1$, $R^2$ and $R^3$ have the same meanings as described in the compound of the formula (II). The compound (III) is available by reducing the cyano group of the compound of the formula (II). The amino group of this compound preferably has a configuration as shown by the following formula:

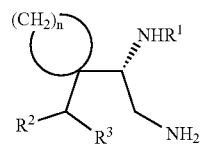

The compound is deacetalized in a similar manner to that employed for the above-described compound, whereby an aldehyde compound represented by the following formula:

III-ALD

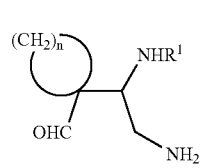

can be obtained.

A compound of the present invention represented by the formula (IV):

IV

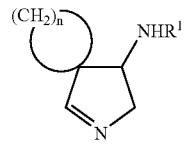

will next be described. In the formula, n and the substituent $R^1$ have the same meanings as described above. The configuration of the amino group is preferably that shown by the following formula:

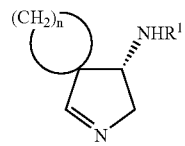

The compound represented by the formula (IV) is available by subjecting, to ring-closure, a compound obtained by converting the acetal of the compound of the formula (III) into an aldehyde.

Reduction of the imino portion of the compound represented by the formula (IV) yields a compound represented by formula (VII):

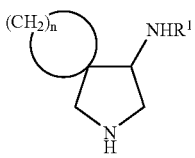

Also in this compound, n and the substituent R¹ in the formula have the same meanings as described above. The configuration of the amino group of this compound is preferably that represented by the following formula:

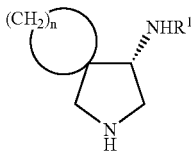

as described above.

The target compound represented by formula (VIII):

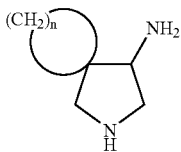

is available by converting the substituent R¹ (except hydrogen) of the compound of the formula (VII) into a hydrogen atom by the ordinarily employed method.

A compound represented by the formula (XI):

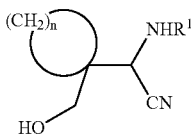

will next be described. In the formula, n stands for an integer of from 2 to 5. The substituent R¹ represents a hydrogen atom or a group represented by formula:

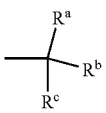

[wherein, $R^a$, $R^b$ and $R^c$ each independently represents a phenyl group, a benzyl group, a naphthyl group (the aryl portion of these groups may have one or more substituents, which may be the same or different in kind, selected from the class consisting of a $C_{1-4}$ alkyl group, a $C_{1-4}$ alkoxy group, a halogen atom and a nitro group), a hydrogen atom, or a $C_{1-4}$ alkyl group].

When the substituent R¹ is a group represented by the following formula:

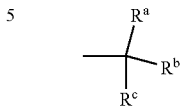

, no limitation is imposed on it insofar as it undergoes no change even by the converting reaction of the cyano group of the compound of the formula (XI) to an aminomethyl group and can protect the amino group.

With regards to the substituent R¹, the inventors of the present application have considered that in order to obtain an isomer having a necessary configuration, the compound of the formula (XI) is preferably a diastereomer-containing structure. The compound of the formula (XI) has, as a carbon to which an amino group is bonded, an asymmetric carbon, meaning that the compound of the formula (XI) has a diastereomer when the substituent R¹ contains an asymmetric carbon. The inventors of the present application have considered that upon preparation of the compound of the formula (XI) which is a mixture of diastereomers, their yields are not uniform and one diastereomer is prepared preferentially to the other diastereomer. Which diastereomer is prepared preferentially can be controlled by the steric structure of the substituent R¹. In other words, it is possible to form a target diastereomer preferentially by changing the structure of the substituent R¹.

The substituent R¹ in which $R^a$, $R^b$ and $R^c$ are different each other is therefore preferred.

Specific examples of the $R^a$, $R^b$ and $R^c$ include a hydrogen atom, and methyl, ethyl, phenyl, 4-methylphenyl, 4-methoxyphenyl, 4-chlorophenyl, 4-nitrophenyl, 2,4-dichlorophenyl, 2,4-dinitrophenyl, 3,5-dichlorophenyl, 3,5-dinitrophenyl and naphthyl groups.

Specific examples of the $C_{1-4}$ alkyl groups, $C_{1-4}$ alkoxy groups, halogen atoms and nitro group which are substituents on the aryl group include methyl group, methoxy group, nitro group and chlorine atom. One or more of the above-exemplified groups or atoms, which may be the same or different in kind, may be substituted on the aryl group.

Examples of the substituent R¹ in which $R^a$, $R^b$, and $R^c$ are different each other include (R)-1-phenylethyl, (S)-1-phenylethyl, (R)-1-phenylpropyl, (S)-1-phenylpropyl, (R)-1-phenyl-2-(p-tolyl)ethyl, (S)-1-phenyl-2-(p-tolyl)ethyl, (R)-1-(1-naphthyl)ethyl, (S)-1-(1-naphthyl)ethyl, (R)-1-(4-methoxyphenyl)ethyl, (S)-1-(4-methoxyphenyl)ethyl, (R)-1-(4-chlorophenyl)ethyl, (S)-1-(4-chlorophenyl)ethyl, (R)-1-(4-nitrophenyl)ethyl, (S)-1 (4-nitrophenyl)ethyl, (R)-1-(2,4-dichlorophenyl)ethyl, (S)-1-(2,4-dichlorophenyl)ethyl, (R)-1-(2,4-dinitrophenyl)ethyl, (S)-1-(2,4-dinitrophenyl)ethyl, (R)-1-(3,5-dichlorophenyl)ethyl, (S)-1-(3,5-dichlorophenyl)ethyl, (R)-1-(3,5-dinitrophenyl)ethyl, and (S)-1-(3,5-dinitrophenyl)ethyl groups. Of these, (R)-1-phenylethyl and (S)-1-phenylethyl are particularly preferred.

The substituent R¹ may be another protecting group of the amino group. In this case, any group is usable insofar as the group does not undergo a change even by the converting reaction of the cyano group of the compound (XI) into an aminomethyl group. Examples of such an amino protecting group include alkoxycarbonyl groups which may have a substituent such as tert-butoxycarbonyl group and 2,2,2-trichloroethoxycarbonyl group, aralkyloxycarbonyl groups which may have a substituent such as benzyloxycarbonyl group, paramethoxybenzyloxycarbonyl group and paranitrobenzyloxycarbonyl group, aliphatic or aromatic acyl groups which may have a substituent such as acetyl group, methoxyacetyl group, trifluoroacetyl group, chloroacetyl group, pivaloyl group, formyl group, and benzoyl group, and aralkyl groups which may have a substituent such as benzyl group, paranitrobenzyl group, paramethoxybenzyl group and triphenylmethyl group.

Of these protecting groups, aralkyl groups are preferred from the viewpoint of preparation ease. Of the aralkyl groups, a benzyl group is more preferred. The phenyl group of the benzyl group may further have a substituent. It may have one or more substituents, which may be the same or different in kind, selected from the group consisting of $C_{1-4}$ alkyl groups, $C_{1-4}$ alkoxy groups, halogen atoms and nitro group. Specific example of the protecting group include, in addition to a benzyl group, 4-methoxybenzyl group, 4-chlorobenzyl group, 4-nitrobenzyl group, 2,4-dichlorobenzyl group, 2,4-dinitrobenzyl group, 3,5-dichlorobenzyl group and 3,5-dinitrobenzyl group.

Of the compounds represented by the formula (XI), the compound whose amino group has a preferably configuration is represented by the following formula:

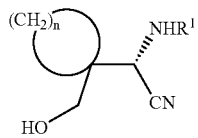

The compound of the formula (XI) may be an acid addition salt. No particular limitation is imposed on the acid forming a salt insofar as it has no influence on the stability of the compound itself. As such an acid, either an inorganic acid or organic acid is usable. Examples of a salt with the inorganic acid include hydrochloride, hydrobromide, nitrate, phosphate and perchlorate, while those of a salt with the organic acid include salts with a carboxylic acid compound and those with a sulfonic acid compound. Examples of the carboxylate include acetate, fumarate and lactate, while those of the sulfonate include methanesulfonate, trifluoromethanesulfonate, benzenesulfonate and toluenesulfonate. These salts may take the form of a hydrate. This will equally apply to the formation of a salt with the below-described compounds.

With regards to the compound of the formula (II-ALD), n, substituent $R^1$ and preferable configuration may be similarly considered to those of the compound of the formula (XI).

The compound represented by the formula (VII) is useful because conversion of it into the compound of the formula (XII) by changing the amino protecting group enables further more substitution reactions. The compound represented by formula (XII):

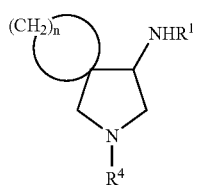

has, as n, an integer of from 2 to 5. $R^1$ has the same meaning as that described in the compound represented by the formula (II). As $R^4$, any group is usable insofar as it does not undergo a change even by the deprotection reaction of $R^1$ and can protect the amino group. It is preferred that $R^4$ and $R^1$ are different groups (protecting groups) and they can be eliminated under different conditions.

$R^4$ represents, for example, an aliphatic or aromatic acyl group, an alkoxycarbonyl group, aralkyloxycarbonyl group, or an aralkyl group. Examples of the acyl group include formyl, acetyl, propanoyl, butyloyl, benzoyl, fluoroacetyl, difluoroacetyl, trifluoroacetyl, chloroacetyl, dichloroacetyl and trichloroacetyl groups. Examples of the alkoxycarbonyl group include methoxycarbonyl, ethoxycarbonyl, tert-butoxycarbonyl, and 2,2,2-trichloroethoxycarbonyl groups. Examples of the aralkyloxycarbonyl group include benzyloxycarbonyl, paramethoxybenzyloxycarbonyl, and paranitrobenzyloxycarbonyl groups. Examples of the aralkyl group include benzyl, paranitrobenzyl, paramethoxybenzyl and triphenylmethyl groups.

A compound represented by formula (XII-a):

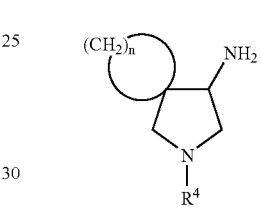

will next be described. In the formula, n stands for an integer of from 2 to 5 and $R^4$ has the same meaning as described in the compound represented by the formula (XII).

A compound represented by formula (XIII):

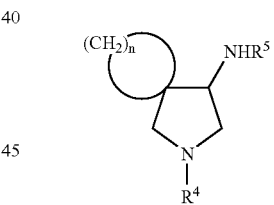

will next be described. In the formula, n stands for an integer of from 2 to 5, and $R^4$ has the same meaning as described in the compound represented by the formula (XII). $R^5$ may be any group insofar as it undergoes no change upon deprotection reaction of $R^4$ and can protect the amino group.

$R^5$ represents, for example, an aliphatic or aromatic acyl group, an alkoxycarbonyl group, aralkyloxycarbonyl group, or an aralkyl group. Examples of the acyl group include formyl, acetyl, propanoyl, butyloyl, benzoyl, fluoroacetyl, difluoroacetyl, trifluoroacetyl, chloroacetyl, dichloroacetyl and trichloroacetyl groups. Examples of the alkoxycarbonyl group include methoxycarbonyl, ethoxycarbonyl, tert-butoxycarbonyl, and 2,2,2-trichloroethoxycarbonyl groups. Examples of the aralkyloxycarbonyl group include benzyloxycarbonyl, paramethoxybenzyloxycarbonyl, and paranitrobenzyloxycarbonyl groups. Examples of the aralkyl group include benzyl, paranitrobenzyl, paramethoxybenzyl and triphenylmethyl groups.

Following are the above-described compounds having a preferable configuration:

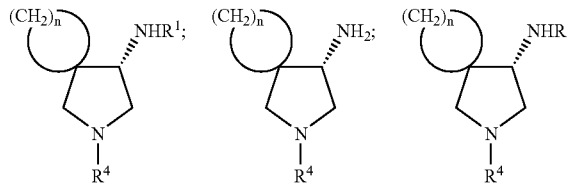

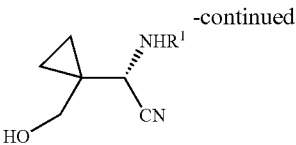
-continued

In the present invention, compounds having, as n, 2 are preferred and such compounds are shown below.

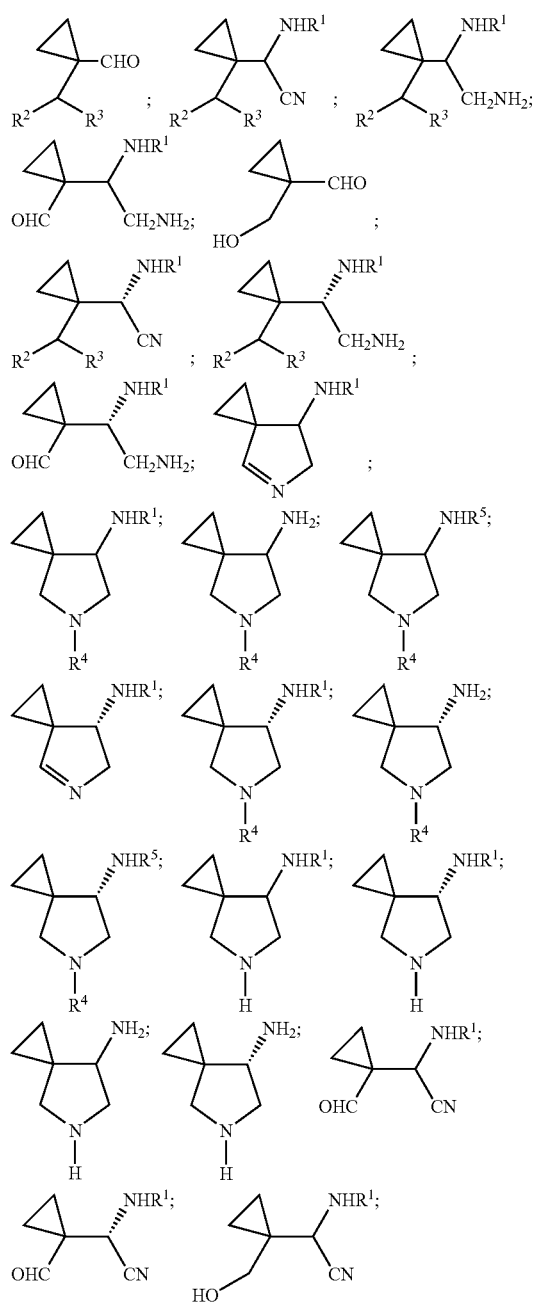

BEST MODE FOR CARRYING OUT THE INVENTION

The present invention will hereinafter be described by Examples. It should however be borne in mind that the present invention is not limited to or by them.

EXAMPLE 1

1-(Diethoxymethyl)-cyclopropane Carboaldehyde (Monoacetal Compound)

In toluene (0.5 ml) was dissolved 1,1-cyclopropane dicarboaldehyde (49 mg, 0.5 mmol). Under ice cooling and stirring, p-toluenesulfonate monohydrate (1.9 mg, 0.01 mmol), ethyl orthoformate (74 mg, 0.5 mmol), and ethanol (23 mg, 0.5 mmol) were added successively. The resulting mixture was stirred at room temperature for 1 hour. A saturated aqueous solution of sodium bicarbonate was added to the reaction mixture, followed by extraction with ethyl acetate. The organic layer was washed successively with water and saturated saline, dried over anhydrous sodium sulfate, filtered, and then evaporated under reduced pressure, whereby a colorless oil (67.9 mg, 78.9%) was obtained. A ratio of the monoacetal compound and diacetal compound was found to be about 40:1 based on an integral ratio of $^1$H-NMR.

$^1$H-NMR ($C_6D_6$) δ: 0.87–1.08 (m, 4H), 1.01 (t, J=6.9 Hz, 6H), 3.25 (q, J=6.9 Hz, 1H), 3.29 (q, J=6.9 Hz, 1H), 3.45 (q, J=6.9 Hz, 1H), 3.48 (q, J=6.9 Hz, 1H), 4.74(s, 1H), 9.29 (s, 1H).

Reference: 1,1-Bis(diethoxymethyl)cyclopropane (diacetal compound)

$^1$H-NMR ($C_6D_6$) δ: 0.91 (s, 4H), 1.10 (t, J=6.9 Hz, 12H), 3.39 (q, J=6.9 Hz, 2H), 3.42 (q, J=6.9 Hz, 2H), 3.61 (q, J=6.9 Hz, 2H), 3.64 (q, J=6.9 Hz, 2H), 4.93 (s, 1H).

EXAMPLE 2

1-(Diethoxymethyl)cyclopropane carboaldehyde

In toluene (260 ml) was dissolved 1,1-cyclopropane dicarboaldehyde (30 g, 306 mmol). The resulting solution was stirred at 20° C. To the reaction mixture was added dropwise a solution of p-toluenesulfonate monohydrate (153 mg, 0.77 mml) in toluene (10 ml) and the mixture was cooled to the internal temperature of 5° C. or less. A solution of ethyl orthoformate (49.7 g, 335 mmol) in toluene (30 ml) was gradually added dropwise. After completion of the dropwise addition, the mixture was stirred continuously for 1 hour over an ice bath. At the internal temperature elevated to 25° C., stirring was conducted for further 1 hour. After completion of the reaction was confirmed, the internal temperature was adjusted to 15° C., at which 2 mol/l-NaOH (3.75 ml) was added, followed by stirring for 1 hour. Water (50 ml) was added and the mixture was separated and extracted. Toluene was then evaporated under reduced pressure, whereby a colorless oil (55.8 g, stoichiometric) was obtained. Concerning a ratio of the monoacetal compound and the diacetal compound, that of the monoacetal compound was found to be 95% or greater. The instrumental analysis data were similar to those described in Example 1.

EXAMPLE 3

1-(Diethoxymethyl)cyclopropane carboaldehyde

In ethanol (2.0 ml) was dissolved 1,1-cyclopropane dicarboaldehyde (200 mg, 2.04 mmol). Anhydrous magnesium sulfate (246 mg, 2.04 mmol) and p-toluenesulfonate monohydrate (19.4 mg, 0.1 mml) were added, followed by stirring at 50° C. for 1 hour. At this point, the reaction mixture was analyzed by gas chromatography, resulting in a ratio of the monoacetal compound to the diacetal compound of about 90:10. The instrumental analysis data were similar to those described in Example 1.

EXAMPLE 4

1-(Diethoxymethyl)cyclopropane carboaldehyde

In ethanol (2.0 ml) was dissolved 1,1-cyclopropane dicarboaldehyde (200 mg, 2.04 mmol). Ethyl orthoformate (59.0 mg, 0.41 mmol) and p-toluenesulfonate monohydrate (19.4 mg, 0.1 mml) were added, followed by stirring at 50° C. for 1 hour. At this point, the reaction mixture was analyzed by gas chromatography, resulting in a ratio of the monoacetal compound to the diacetal compound of about 90:10. The instrumental analysis data were similar to those described in Example 1.

EXAMPLE 5

2-(Benzylamino)-2-[1-(diethoxymethyl)cyclopropyl] acetonitrile

In toluene (30 ml) was dissolved 1,1-cyclopropane dicarboaldehyde (2.94 g, 30 mmol). Under ice cooling and stirring, a solution of p-toluenesulfonate monohydrate (5.7 mg, 0.03 mmol) in ethanol (138 mg, 3.0 mmol), and then, ethyl orthoformate (4.67 g, 31.5 mmol) were added. The resulting mixture was stirred at the external temperature of 40° C. for 1 hour. After addition of a saturated aqueous solution (3 ml) of sodium bicarbonate to the reaction mixture, benzyl amine (3.54 g, 33 mmol) was added under ice cooling and stirring. At the same temperature, the mixture was stirred for 30 minutes. To the reaction mixture were added successively potassium cyanide (2.15 g, 33 mmol) and sodium bisulfite (4.69 g, 45 mmol), and then water (30 ml). The resulting mixture was stirred at room temperature for 13 hours. A saturated aqueous solution of sodium bicarbonate was added, followed by extraction with ethyl acetate. The organic layer was washed successively with water and saturated saline, dried over anhydrous sodium sulfate, filtered, and then evaporated under reduced pressure. The pale yellow oil thus obtained was subjected to chromatography on a silica gel column (silica gel; 150 g, hexane:ethyl acetate=10:1.) to give a colorless oil as the title compound (6.16 g, 71.2%).

$^1$H-NMR (C$_6$D$_6$) δ: 0.33–1.00 (m, 4H), 0.97 (t, J=6.9 Hz, 6H), 3.10–3.29 (m, 2H), 3.31–3.47 (m, 2H), 3.46 (s, 1H), 3.61 (d, J=13.2 Hz, 1H), 3.83 (d, J=13.2 Hz, 1H), 4.69 (s, 1H), 7.09–7.27 (m, 5H).

FABMS (m/z); 289 (M$^+$+H), 243, 217

EXAMPLE 6

(2S)-2-[1-(Diethoxymethyl)cyclopropyl]-2-{[(1S)-1-phenylethyl]amino}acetonitrile In toluene (20 ml) was dissolved 1,1-cyclopropane dicarboaldehyde (1.96 g, 20 mmol). Under ice cooling and stirring, a solution of p-toluenesulfonate monohydrate (19.2 mg, 0.1 mmol) in ethanol (276 mg, 6.0 mmol), and then ethyl orthoformate (3.11 g, 21 mmol) were added. The mixture was stirred at the external temperature of 40° C. for 1 hour. After addition of a saturated aqueous solution (0.3 ml) of sodium bicarbonate to the reaction mixture, (S)-1-phenylethylamine (2.67 g, 22 mmol) was added under ice cooling and stirring. At the same temperature, stirring was conducted for 30 minutes. To the reaction mixture were successively added potassium cyanide (1.43 g, 22 mmol) and sodium bisulfite (3.12 g, 30 mmol). Then, water (20 ml) was added and the mixture was stirred at 50° C. for 2 hours. A saturated aqueous solution of sodium bicarbonate was added, followed by extraction with ethyl acetate. The organic layer was washed successively with water and saturated saline, dried over anhydrous sodium sulfate, filtered, and then evaporated under reduced pressure. The yellow oil thus obtained was subjected to chromatography on a silica gel column (silica gel: 100 g, hexane:ethyl acetate=from 10:1 to 5:1), whereby a mixture (3.86 g, 63.9%) of the title compound and its diastereomer, (2R)-2-[1-(diethoxymethyl)cyclopropyl]-2-{[(1S)-1-phenylethyl]amino}acetonitrile was obtained as colorless crystals. A formation ratio of these two diastereomers was found to be 2:1 based on the integral ratio of $^1$H-NMR (the title compound was a main product).

$^1$H-NMR (C$_6$D$_6$) δ: 0.14–0.60 (m, 4H), 0.88–1.05 (m, 6H), 1.14 (d, J=6.4 Hz, 3H×2/3), 1.16 (d, J=6.4 Hz, 3H×1/3), 3.07–3.50 (m, 4H), 3.17 (s, 1H×2/3), 3.59 (s, 1H×1/3), 4.01–4.13 (m, 1H), 4.61 (x, 1H×1/3), 4.79 (s, 1H×2/3), 7.05–7.34 (m, 5H).

FABMS (m/z); 303 (M$^+$+H), 257, 230, 105

EXAMPLE 7

(2S)-2-[1-(Diethoxymethyl)cyclopropyl]-2-{[(1S)-1-naphthylethyl]amino}acetonitrile In toluene (3.0 ml) was dissolved 1,1-cyclopropane dicarboaldehyde (294 mg, 3.0 mmol). Under ice cooling and stirring, a solution of p-toluenesulfonate monohydrate (2.9 mg, 0.015 mmol) in ethanol (41.5 mg, 0.9 mmol), and then ethyl orthoformate (467 mg, 3.2 mmol) were added. The mixture was stirred at the external temperature of 40° C. for 1 hour. After addition of a saturated aqueous solution (0.3 ml) of sodium bicarbonate to the reaction mixture, (S)-1-naphthylethylamine (565 mg, 3.3 mmol) was added under ice cooling and stirring. At the same temperature, stirring was conducted for 30 minutes. To the reaction mixture were successively added potassium cyanide (215 mg, 3.3 mmol) and sodium bisulfite (469 mg, 4.5 mmol). Then, water (3.0 ml) was added and the mixture was stirred at 50° C. for 2 hours. A saturated aqueous solution of sodium bicarbonate was added, followed by extraction with ethyl acetate. The organic layer was washed successively with water and saturated saline, dried over sodium sulfate, filtered, and then evaporated under reduced pressure. The yellow oil (1.19 g) thus obtained was subjected to chromatography on a silica gel column (silica gel: 36 g, hexane:ethyl acetate=from 10:1 to 5:1), whereby a mixture (732 mg, 69.2%) of the title compound and its diastereomer, (2R)-2-[1-(diethoxymethyl)cyclopropyl]-2-{[(1S)-1-naphthylethyl]amino}acetonitrile was obtained as a colorless oil. A formation ratio of these two diastereomers was found to be 1.6:1 based on the integral ratio of $^1$H-NMR (the title compound was a main product).

$^1$H-NMR (C$_6$D$_6$) δ: 0.14–0.97 (m, 4H), 0.89–1.04 (m, 6H), 1.33 (d, J=6.6 Hz, 3H×1.6/2.6), 1.34 (d, J=6.6 Hz, 3H×1.0/2.6), 3.06–3.50 (m, 4H), 3.18 (s, 1H×1.6/2.6), 3.67 (s, 1H×1.0/2.6), 4.59 (s, 1H×1.0/2.6), 4.83 (s, 1H×1.6/2.6), 4.93–4.97 (m, 1H) 7.24–8.42 (m, 7H).

FABMS (m/z); 353 (M$^+$+H), 307, 280, 155

EXAMPLE 8

(2S)-2-[1-(Diethoxymethyl)cyclopropyl]-2-{[(1S)-1-phenyl-2-(p-tolyl)ethyl]amino}acetonitrile In toluene (3.0 ml) was dissolved 1,1-cyclopropane dicarboaldehyde (294 mg, 3.0 mmol). Under ice cooling and stirring, a solution of p-toluenesulfonate monohydrate (2.9 mg, 0.015 mmol) in ethanol (41.5 mg, 0.9 mmol), and then ethyl orthoformate (467 mg, 3.2 mmol) were added. The mixture was stirred at the external temperature of 40° C. for 1 hour. After addition of a saturated aqueous solution (0.3 ml) of sodium bicarbonate to the reaction mixture, (S)-1-phenyl-2-(p-tolyl)ethylamine (697 mg, 3.3 mmol) was added under ice cooling and stirring. At the same temperature, stirring was conducted for 30 minutes. To the reaction mixture were successively added potassium cyanide (215 mg, 3.3 mmol) and sodium bisulfite (469 mg, 4.5 mmol). Then, water (3.0 ml) was added and the mixture was stirred at 50° C. for 2 hours. A saturated aqueous solution of sodium bicarbonate was added, followed by extraction with ethyl acetate. The organic layer was washed successively with water and saturated saline, dried over sodium sulfate, filtered, and then evaporated under reduced pressure. The yellow oil (1.22 g) thus obtained was subjected to chromatography on a silica gel column (silica gel: 36 g, hexane:ethyl acetate=from 10:1 to 5:1), whereby a mixture (715 mg, 60.7%) of the title compound and its diastereomer, (2R)-2-[1-(diethoxymethyl)cyclopropyl]-2-{[(1S)-1-phenyl-2-(p-tolyl)ethyl]amino}acetonitrile was obtained as a colorless oil. A formation ratio of these two diastereomers was found to be 2.2:1 based on the integral ratio of $^1$H-NMR (the title compound was a main product).

$^1$H-NMR (C$_6$D$_6$) δ: 0.03–0.54 (m, 4H), 0.85–1.04 (m, 6H), 2.06 (s, 3H×1.0/3.2), 2.08 (s, 3H×2.2/3.2), 2.73–2.92 (m, 2H), 3.03–4.63 (m, 4H and 1H), 4.18 (m, 1H×1.0/3.2), 4.39 (m, 1H×2.2/3.2), 4.46 (s, 1H×1.0/3.2), 4.76 (s, 1H×2.2/3.2), 6.90–7.39 (m, 9H).

FABMS (m/z); 393 (M$^+$+H), 347, 320, 195

EXAMPLE 9

Epimerization of (2R)-2-[1-(Diethoxymethyl)cyclopropyl]-2-{[(1S)-1-phenylethyl]amino}acetonitrile Anhydrous ethanol (1.0 ml) was added to a mixture of the title compound and its diastereomer, (2S)-2-[1-(diethoxymethyl)cyclopropyl]-2-{[(1S)-1-phenylethyl]amino}acetonitrile (the mixture: 16 mg, mixing ratio=1:1.8, (2S)-2-[1-(diethoxymethyl)cyclopropyl]-2-{[(1S)-1-phenylethyl]amino}acetonitrile was a main component). After stirring at 60° C. for 30 minutes in an argon gas stream, the reaction mixture was concentrated under reduced pressure. The diastereomer mixing ratio of the reuslting colorless crystals (16 mg) was found to be 3.4:1 based on the integral ratio of $^1$H-NMR ((2S)-2-[1-(diethoxymethyl)cyclopropyl]-2-{[(1S)-1-phenylethyl]amino}acetonitrile was a main component).

EXAMPLE 10

Purification of (2S)-2-[1-(diethoxymethyl)cyclopropyl]-2-{[(1S)-1-phenylethyl]amino}acetonitrile Anhydrous ethanol (1.5 ml) was added to a diastereomer mixture of (2S)-2-[1-(diethoxymethyl)cyclopropyl]-2-{[(1S)-1-phenylethyl]amino}acetonitrile and (2R)-2-[1-(diethoxymethyl)cyclopropyl]-2-{[(1S)-1-phenylethyl]amino}acetonitrile (the mixture: 300 mg, diastereomer ratio=2:1, the title compound was a main component). After stirring at 60° C. for 30 minutes in an argon gas stream, the reaction mixture was allowed to cool down to room temperature. Under ice cooling, stirring was performed for 1 hour. The crystals thus precipitated were collected by filtration and title compound (first crystals: 200 mg, 66.6%) was obtained as colorless needle crystals. The mother liquid was concentrated under reduced pressure and the crystal residue (93 mg) thus obtained was subjected to a similar operation to the above-described one, whereby the title compound (second crystals: 37 mg, 12.4%) was obtained as colorless needle crystals. HPLC analysis revealed that the resulting crystals had an optical purity of 99.9% de.

Melting point (EtOH): 96 to 97° C.

$^1$H-NMR (C$_6$D$_6$) δ: 0.14–0.60 (m, 4H), 0.93 (t, J=6.9 Hz, 3H), 1.00 (t, J=6.9 Hz, 3H), 1.14 (d, J=6.6 Hz, 3H), 3.07–3.31 (m, 2H), 3.17 (s, 1H), 3.36–3.50 (m, 2H), 4.12 (q, J=6.6 Hz, 1H), 4.79 (s, 1H), 7.05–7.34 (m, 5H).

FABMS (m/z); 303 (M$^+$+H), 257, 230, 105

(HPLC conditions)
Column; CHIRALCEL-OJ (4.6 mmØ×250 mm)
Mobile phase; hexane:isopropanol=98:2
Flow rate; 0.5 ml/min
Temperature; room temperature
Detection; UV 254 nm
Retention time; (S)-form: 9.4 minutes, (R)-form: 10.4 minutes
Analysis results of the resulting compound;
9.4 minutes: >99% ((S,S)-form) 10.4 minutes: <1% ((R, S)-form)

EXAMPLE 11

(2S)-2-[1-(Diethoxymethyl)cyclopropyl]-2-{[(1S)-1-phenylethyl]amino}acetonitrile In ethanol (240 ml) was dissolved 1-(diethoxymethyl)cyclopropane carboaldehyde (30.0 g, 306 mmol). The mixture was stirred at 0° C. for 30 minutes. To the reaction mixture was added dropwise (S)-phenylethylamine (43.5 ml, 336 mmol) and the temperature was elevated to 40° C. At the same temperature, stirring was conducted for 30 minutes. Acetone cyanhydrin (33.4 ml, 367 mmol) was added dropwise and the mixture was stirred at the same temperature for 30 minutes. HPLC analysis revealed that a ratio, upon completion of the reaction, between the title compound and its diastereomer, that is, (2R)-2-[1-(diethoxymethyl)cyclopropyl]-2-{[(1S)-1-phenylethyl]amino}acetonitrile was 77:23 (54% de) (the title compound was a main product). Then, water (240 ml) was added dropwise at 40° C. While maintaining the temperature at 40° C., stirring was conducted for 3 hours. After cooling to 20° C., water (30 ml) was added to the reaction mixture, followed by stirring at 20° C. for 14 hours. The reaction mixture was cooled to 0° C., at which stirring was conducted for 3 hours. The crystals thus precipitated were collected by filtration, whereby the title compound (86.2 g, 93%) was obtained as colorless needle crystals. HPLC analysis revealed that the resulting crystals had an optical purity of 99% de.

The instrumental analysis data of the product were similar to those described in Example 6.

EXAMPLE 12

Epimerization of (2R)-2-[1-(diethoxymethyl)cyclopropyl]-2-{[(1S)-1-naphthylethyl]amino}acetonitrile Anhydrous ethanol (1.0 ml) was added to a mixture of the title compound and (2S)-2-[1-(diethoxymethyl)cyclopropyl]-2-{[(1S)-1-naphthylethyl]amino}acetonitrile (the mixture: 30 mg, a diastereomer ratio=10:1, the title compound was a main component). The resulting mixture was stirred under heating at the external temperature of 60° C. for 1 hour in an argon gas stream. The reaction mixture was then concentrated under reduced pressure. The diastereomer mixing ratio of the resulting colorless oil (28 mg) was found to be 2.9:1 based on the integral ratio of $^1$H-NMR ((2S)-2-[1-(diethoxymethyl)cyclopropyl]-2-{[(1S)-1-naphthylethyl] amino}acetonitrile was a main component).

EXAMPLE 13

N-{2-Amino-(1S)-1-[1-(diethoxymethyl)cyclopropyl]ethyl}-N-[(1S)-1-phenylethyl]amine In ethanol (9.0 ml) was dissolved (2S)-2-[1-(diethoxymethyl)cyclopropyl]-2-{[(1S)-1-phenylethyl] amino}acetonitrile (150 mg, 0.496 mmol). To the resulting solution were added a 5 mol/l aqueous solution of sodium hydroxide (0.5 ml, 2.5 mmol) and Raney-nickel (R-100, 1.5 g) were added and the mixture was stirred at room temperature for 5 hours in a hydrogen gas stream. The catalyst was filtered off and the residue was washed with ethanol. The filtrate was concentrated under reduced pressure. Water and chloroform were added to the residue for separation. The organic layer was dried over sodium sulfate, filtered, and then evaporated under reduced pressure, whereby the title compound (150 mg, 98.4%) was obtained as a slightly yellow oil.

$^1$H-NMR (CDCl$_3$) δ: 0.18–0.58 (m, 4H), 1.07–1.28 (m, 6H), 1.31 (d, J=6.4 Hz, 3H), 1.98 (t, J=6.4 Hz, 1H), 2.82 (dd, J=3.0 and 6.4 Hz, 2H), 3.35–3.72 (m, 4H), 3.93 (q, J=6.4 Hz, 1H), 4.32 (s, 1H), 7.19–7.32 (m, 5H).

EIMS (m/z); 276 (M$^+$—CH$_2$NH$_2$), 230, 105

EXAMPLE 14

(S)-N-[(S)-Phenylethyl]-5-azaspiro[2.4]hept-4-en-7-amine

In acetone (1.0 ml) was dissolved (S)-N-{2-amino-1-[1-(diethoxymethyl)cyclopropyl]ethyl}-N-[(S)-1-phenylethylamine] (136 mg). Under ice cooling and stirring, 1 mol/l hyrochloric acid (2.0 ml) was added and the mixture was stirred at room temperature for 1 hour. Toluene was added to the reaction mixture for separation. Under ice cooling and stirring, a saturated aqueous solution of sodium bicarbonate was added to the water layer to make it alkaline, followed by extraction with ethyl acetate. The organic layer was washed successively with water and saturated saline, dried over sodium sulfate, filtered, and then evaporated under reduced pressure, whereby the title compound (85 mg, 90.0%) was obtained as a slightly yellow oil.

$^1$H-NMR (CDCl$_3$) δ: 0.67–0.74 (m, 1H), 0.82–0.97 (m, 2H), 1.18–1.26 (m, 1H), 1.30 (d, J=6.4 Hz, 3H), 2.85 (dd, J=4.0 and 6.9 Hz, 1H), 3.82 (q, J=6.4 Hz, 1H), 3.86 (dd, J=4.0 and 15.8 Hz, 1H), 4.09 (dd, J=6.9 and 15.8 Hz, 1H), 6.98 (s, 1H), 7.18–7.35 (m, 5H).

EIMS (m/z); 214 (M$^+$), 109, 105

EXAMPLE 15

(S)-N-[(S)-1-Phenylethyl]-5-[2,4]hept-4-en-7-amine

In ethanol (2.6 ml) was dissolved (S)-N-[(S)-1-phenylethyl]-5-azaspiro[2.4]hept-4-en-7-amine (85 mg, 0.40 mmol). Raney nickel (R-100, 427 mg) was added and the mixture was stirred at room temperature for 2 hours in a hydrogen gas stream. The catalyst was filtered off and the residue was washed with ethanol. The filtrate was concentrated under reduced pressure. To the residue were added a 0.5 mol/l aqueous solution of sodium hydroxide and chloroform for separation. The organic layer was dried over sodium sulfate, filtered, and then evaporated under reduced pressure, whereby the title compound (71 mg, 82.9%) was obtained as a slightly yellow oil.

$^1$H-NMR (CDCl$_3$) δ: 0.41–0.50 (m, 3H), 0.68–0.80 (m, 1H), 1.32 (d, J=6.6 Hz, 3H), 2.47 (dd, J=3.3 and 5.0 Hz, 1H), 2.68 (d, J=10.9 Hz, 1H), 2.93 (dd, J=3.3 and 11.2 Hz, 1H), 3.07 (d, J=10.9 Hz, 1H), 3.10 (dd, J=5.0 and 11.2 Hz, 1H), 3.74 (q, J=6.6 Hz, 1H), 7.19–7.35 (m, 5H).

EIMS (m/z); 216 (M$^+$), 187, 111, 105

EXAMPLE 16

In a similar manner to Referential Example 1, 5-[2.4] heptane-(S)-7-amine was synthesized using the (S)-N-[(S)-1-phenylethyl]-5-azaspiro[2.4]heptane-7-amine obtained in Example 15 and its optical purity was measured. The measurement of the optical purity was conducted as follows.

The resulting compound a racemic modification were dissolved in tetrahydrofuran, followed by the addition of 3,5-dinitrobenzoyl chloride. Under ice cooling, triethylamine was added dropwise and the resulting mixture was stirred at room temperature for 30 minutes. The reaction mixture was separated by the addition of a saturated aqueous solution of sodium bicarbonate and ethyl acetate. The organic layer was analyzed by HPLC.

(HPLC conditions)
Column; SUMICHIRALOA-4600 (4.6 mmØ×250 mm)
Mobile phase; hexane:1,2-dichloroethane:ethanol 60:40:5
Flow rate; 1.0 ml/min
Temperature; room temperature
Detection; UV 254 nm
Retention time; (S)-form: 6.8 minutes, (R)-form: 10.0 minutes
Analysis results of the resulting compound;
6.8 minutes: 99% ((S)-form) 10.0 minutes: 1% ((R)-form)

REFERENTIAL EXAMPLE 1

5-Azaspiro[2.4]heptane-(S)-7-amine dihydrochloride

In an autoclave were charged (S)-N-[(S)-1-phenylethyl]-5-azaspiro[2.4]heptane-7-amine (79 mg, 0.36 mmol), 20% Pd(OH)$_2$—C (50% wet, 37 mg), ethanol (2.0 ml), water (1.0 ml) and concentrated hydrochloric acid (0.5 ml), followed by stirring overnight at room temperature in a hydrogen gas atmosphere (3.92 Mpa (40 kgf/cm$^2$). After reaction, the catalyst was filtered off and the filtrate was concentrated under reduced pressure, whereby colorless crystals (72 mg, 82%) was obtained.

REFERENTIAL EXAMPLE 2

[1-(Diethoxymethyl)cyclopropyl]methanol

A tetrahydrofuran (190 mL) solution of 1-(diethoxymethyl)cyclopropane carboaldehyde (37.78 g) was cooled to 0° C. Lithium aluminum hydride (2 g, 52.7 mmol) was added and the mixture was stirred for 40 minutes. Water was added to terminate the reaction, followed by extraction with chloroform. The organic layer was washed with water and then dried over sodium sulfate. The solvent was evaporated under reduced pressure, whereby 34.60 g (91%) of the title compound was obtained as a colorless oil.

$^1$H-NMR (CDCl$_3$) δ: 4.30 (1H, s), 3.79–3.68 (2H, m), 3.60–3.49 (2H, m), 3.54 (2H, d, J=5.6 Hz), 2.79 (1H, t, J=5.6 Hz), 1.22 (3H, t, J=7.0 Hz), 0.67–0.63 (2H, m), 0.50–0.46 (2H, m).

REFERENTIAL EXAMPLE 3

1-(Hydroxymethyl)cyclopropane carboaldehyde

An acetone (73 mL) solution of [1-(diethoxymethyl)cyclopropyl]methanol (34.6 g, 199 mmol) was cooled to 0° C. To the reaction mixture was added 1.2 mol/l hydrochloric acid (10 ml) and the mixture was stirred for 30 minutes. The reaction was terminated by the addition of a 1 mol/l aqueous solution (12 mL) of sodium hydroxide, followed by extraction with chloroform. The organic layer was washed with water and then dried over sodium sulfate. The solvent was evaporated under reduced pressure, whereby 16.6 g (83%) of the title compound was obtained as a pale yellow oil.

$^1$H-NMR (CDCl$_3$) δ: 8.77 (1H, s), 3.74 (2H, s), 3.13 (1H, brs), 1.28–1.21 (2H, m), 1.19–1.12 (2H, m).

EXAMPLE 17

2-[1-(Hydroxymethyl)cyclopropyl-2-{[(1S)-1-phenylethyl]amino}acetonitrile

To an ethanol (4.9 mL) solution of 1-(hydroxymethyl) cyclopropane carboaldehyde (683 mg, 6.82 mmol) were added water (2.1 mL), (S)-(−)-1-phenylethylamine (0.94 mL, 7.50 mmol), potassium cyanide (489 mg, 7.50 mmol) and sodium bisulfite (1.45 g, 13.6 mmol). The mixture was stirred at 50° C. for 30 minutes. After cooling to 0° C., a saturated aqueous solution of sodium bicarbonate was added to terminate the reaction, followed by extraction with ethyl acetate. The organic layer was washed with water and then dried over magnesium sulfate. The solvent was and evaporated under reduced pressure, whereby the title compound was obtained as a pale yellow oil (1.55 g, crude product).

$^1$H-NMR (CDCl$_3$, main product) δ: 7.38–7.30 (5H, m), 4.05 (1H, q, J=6.6 Hz), 3.56 (2H, s), 3.44 (1H, s), 1.43 (3H, d, J=6.6 Hz), 0.71–0.54 (4H, m).

EXAMPLE 18

2-(1-Formylcyclopropyl)-2-{[(1S)-1-phenylethyl]amino}acetonitrile

Pyridinium chlorochromate (3.74 g, 17.4 mmol) was added to a dichloromethane (20 mL) solution of 2-[1-(hydroxymethyl)cyclopropyl-2-{[(1S)-1-phenylethyl]amino}acetonitrile (2.08 g). The resulting mixture was stirred at room temperature for 2 hours. After removal of an insoluble matter by filtration through a silica gel, the solvent was evaporated under reduced pressure. The residue was purified by column chromatography, whereby the title compound was obtained as pale yellow crystals (508 mg, 20% from 1-(hydroxymethyl)cyclopropane carboaldehyde).

$^1$H-NMR (CDCl$_3$, main product) δ: 8.79 (1H, s), 7.36–7.26 (5H, m), 4.07 (1H, q, J=6.4 Hz), 2.04 (1H, s), 1.39 (3H, d, J=6.4 Hz), 1.38–1.07 (4H, m).

EXAMPLE 19

2-(Benzylamino)-2-(1-formylcyclopropyl)acetonitrile

Benzylamine (107 mg, 1.0 mmol) was suspended in a mixture of ethanol (0.5 ml) and water (1.5 ml). To the resulting suspension were successively added potassium cyanide (65 mg, 1.0 mmol) and sodium bisulfite (104 mg, 1.0 mmol) under ice cooling and stirring. An ethanol (1.5 ml) solution of 1,1-cyclopropane dicarboaldehyde (98 mg, 1.0 mmol) was added dropwise and the mixture was stirred at the same temperature for 2 hours. A saturated aqueous solution of sodium bicarbonate was added to the reaction mixture, followed by extraction with ethyl acetate. The organic layer was washed successively with water and saturated saline, dried over sodium sulfate, filtered, and then evaporated under reduced pressure. The oily residue thus obtained was subjected to chromatography on a silica gel column (silica gel 8.0 g; hexane:ethyl acetate=5:1), whereby the title compound (109 mg, 50.8%) was obtained as a slightly yellow oil.

$^1$H-NMR (CDCl$_3$) δ: 1.21–1.38 (m, 4H), 3.52 (s, 1H), 3.83 (d, J=13.2 Hz, 1H), 4.11 (d, J=13.2 Hz, 1H), 7.27–7.38 (m, 5H), 8.82 (s, 1H).

EI MS (m/z); 214 (M$^+$), 187, 159, 123

In addition, 2-(benzylamino)-2-{1-[benzylamino]-2-nitroethyl}cyclopropyl}acetonitrile (53.8 mg, 16.3%) was obtained as colorless crystals.

$^1$H-NMR (CDCl$_3$) δ: 0.81–1.01 (m, 4H), 3.73 (d, J=12.9 Hz, 2H), 4.03 (d, J=12.9 Hz, 2H), 4.19 (s, 2H), 7.21–7.35 (m, 10H).

EXAMPLE 20

(2S)-2-[1-(Diethoxymethyl)cyclopropyl]-2-{[(1S)-1-phenylethyl]amino}acetonitrile Triethyl orthoformate (0.2 mL, 1.20 mmol) and p-toluenesulfonate monohydrate (1 mg, 0.0053 mmol) were added to an ethanol (2.5 mL) solution of 2-(1-formylcyclopropyl)-2-{[(1S)-1-phenylethyl]amino}acetonitrile (102 mg, 0.447 mmol). The resulting mixture was stirred at room temperature for 2 hours and 30 minutes and then, at 50° C. for 4 hours. After cooling to room temperature, a saturated aqueous solution of sodium bicarbonate was added, followed by extraction with ethyl acetate. The organic layer was washed with water and then, dried over sodium sulfate. The solvent was evaporated under reduced pressure. The residue was purified by column chromatography, whereby the title compound was obtained as white crystals (40 mg, 30%, diastereomer ratio=81/19).

$^1$H-NMR (C$_6$D$_6$, main product) δ: 0.14–0.60 (m, 4H), 0.93 (t, J=6.9 Hz, 3H), 1.00 (t, J=6.9 Hz, 3H), 1.14 (d, J=6.6 Hz, 3H), 3.07–3.31 (m, 2H), 3.17 (s, 1H), 3.36–3.50 (m, 2H), 4.12 (q, J=6.6 Hz, 1H), 4.79 (s, 1H), 7.05–7.34 (m, 5H).

EXAMPLE 21

7-(S)-[1-(S)-Phenylethylamino]-5-N-acetylazaspiro[2.4]heptane

In ethyl acetate (20 ml) was dissolved 7-(S)-[(S)-1-phenylethylamino]-5-azaspiro[2.4]heptane (2.16 g, 10 mmol). Under ice cooling and stirring, acetic anhydride (1.02 g, 10 mmol) was added dropwise and the mixture was stirred at the same temperature for 1 hour. The reaction mixture was separated by the addition of a saturated aqueous solution of sodium bicarbonate. The organic layer was washed successively with water and saturated saline. The organic layer was dried over sodium sulfate, filtered, and then evaporated under reduced pressure, whereby the title compound (2.53 g, 98%) was obtained as a slight yellow oil.

$^1$H-NMR (CDCl$_3$) δ: 0.45–0.57 (m, 3H), 0.65–0.71 (m, 1H), 1.30 and 1.33 (d, J=6.6 Hz, 3H, rotamers), 2.00 and 2.06 (s, 3H, rotamers), 2.52 and 2.64 (m, 1H, rotamers), 3.11–3.67 (m, 4H), 3.77 and 3.79 (q, J=6.6 Hz, 1H, rotamers), 7.19–7.36 (m, 5H).

FAB MS (m/z); 259 (M$^+$+H), 217, 155, 105

EXAMPLE 22

7-(S)-Amino-5-N-acetylazaspiro[2.4]heptane (Process 1)

In ethanol (8.0 ml) was dissolved in 7-(S)-[1-(S)-phenylethylamino]-5-N-acetylazaspiro[2.4]heptane (517 mg, 2.0 mmol), followed by the addition of 5% Pd—C (50% wet, 1.03 g). In a hydrogen gas stream, the resulting mixture was stirred at room temperature for 5 hours and then at 50° C. for 3 hours. The catalyst was filtered off and the filtrate was washed with ethanol. The filtrate was then concentrated under reduced pressure, whereby the title compound (365 mg, quant.) was obtained as a colorless oil.

$^1$H-NMR (CDCl$_3$) δ: 0.51–0.80 (m, 4H), 2.02 and 2.07 (s, 3H, rotamers), 3.03–3.46 (m, 3H), 3.60–3.89 (m, 2H).

FAB MS (m/z); 155 (M$^+$+H), 138, 96

EXAMPLE 23

7-(S)-Amino-5-N-acetylazaspiro[2.4]heptane (Process 2)

In dichloromethane (12 ml) was dissolved 7-(S)-amino-5-azaspiro[2.4]heptane (586 mg, 5.0 mol). The resulting solution was cooled to −75° C. Under stirring, a dichloromethane solution of acetic anhydride (510 mg, 5.0 mmol) was added dropwise over 15 minutes and the resulting mixture was stirred at the same temperature for 30 minutes. The solvent was then evaporated under reduced pressure. The residue was separated by the addition of hydrochloric acid and chloroform. An aqueous solution of sodium hydroxide was added to the water layer to make it alkaline, followed by extraction with chloroform. The organic layer was dried over sodium sulfate, filtered, and then evaporated under reduced pressure to give the title compound (707 mg, 92%) as a yellow oil.

EXAMPLE 24

7-(S)-[tert-butoxycarbonylamino]-5-N-acetylazaspiro[2.4]heptane

In ethanol (6.0 ml) was dissolved 7-(S)-amino-5-N-acetylazaspiro[2.4]heptane (365 mg, 2.0 mmol). Triethylamine (304 mg, 3.0 mmol) was added at room temperature, followed by the addition of di-tert-butyl dicarbonate (524 mg, 2.4 mmol). At the same temperature, the resulting mixture was stirred for 2 hours. The solvent was evaporated under reduced pressure. The residue was separated by the addition of chloroform and a saturated aqueous solution of sodium bicarbonate. The organic layer was dried over sodium sulfate, filtered, and then evaporated under reduced pressure to give the title compound (586 mg, quant.) as a crystalline residue.

$^1$H-NMR (CDCl$_3$) δ: 0.53–0.95 (m, 4H), 1.44 and 1.45 (s, 9H, rotamers), 2.02 and 2.06 (s, 2H, rotamers), 3.19–3.30 (m, 1H), 3.60–3.84 (m, 4H).

FAB MS (m/z); 255 (M$^+$+H), 213, 199, 157, 155, 96.

m.p.: 141–142° C. (toluene)

EXAMPLE 25

7-(S)-[tert-Butoxycarbonylamino]-5-[2.4]heptane

In ethanol (4.0 ml) was dissolved 7-(S)-[tert-butoxycarbonylamino]-5-N-acetylazaspiro[2.4]heptane (386 mg, 1.5 mmol). At room temperature, a 1 mol/l aqueous solution (4.0 ml) of sodium hydroxide was added to the resulting solution. After stirring the mixture at 50° C. for 3 hours, a 5 mol/l aqueous solution (2.2 ml) of sodium hydroxide was added thereto, followed by stirring at 70° C. for 20 hours. Ethanol was evaporated under reduced pressure. The residue was separated by the addition of chloroform and water. The organic layer was dried over sodium sulfate, filtered, and then evaporated under reduced pressure, whereby the title compound (231 mg, 72%) was obtained as a crystalline residue. The $^1$H-NMR spectrum of the compound coincided with that of the standard product.

EXAMPLE 26

The measurement of the optical purity of the 7-(S)-[tert-butoxycarbonylamino]-5-azaspiro[2.4]heptane obtained in Example 25 was conducted as follows.

The resulting compound and racemic modification were dissolved in tetrahydrofuran, followed by the addition of 3,5-dinitrobenzoyl chloride. Under ice cooling, triethylamine was added dropwise and the resulting mixture was stirred at room temperature for 30 minutes. The reaction mixture was separated by the addition of a saturated aqueous solution of sodium bicarbonate and chloroform. The organic layer was analyzed by HPLC.

(HPLC conditions)
Column; SUMICHIRAL OA-4400 (4.6 mmØ×250 mm)
Mobile phase; hexane:1,2-dichloroethane:ethanol=75:25:1
Flow rate; 1.0 ml/min
Temperature; room temperature
Detection; UV 254 nm
Retention time; (S)-form: 9.0 minutes, (R)-form: 10.4 minutes
Analysis results of the resulting compound;
(S)-form: 99.2%
(R)-form: 0.8%

EXAMPLE 27

7-(S)-[Benzyloxycarbonylamino]-5-N-acetylazaspiro[2.4]heptane

In dichloromethane (24 ml) was dissolved 7-(S)-amino-5-N-acetylazaspiro[2.4]heptane (2.44 g, 15.8 mmol). Under ice cooling and stirring, triethylamine (1.76 g, 17.4 mmol) was added, followed by the dropwise addition of a dichloromethane solution of benzyloxycarbonyl chloride (2.70 g, 15.8 mmol). At the same temperature, the resulting mixture was stirred for 1 hour. The reaction mixture was separated by the addition of water. The organic layer was concentrated under reduced pressure. The residue was separated by the addition of ethyl acetate and water. The organic layer was dried over sodium sulfate, filtered, and then evaporated under reduced pressure to give a yellow oil (2.64 g). The resulting oil was purified by silica gel column, whereby the title compound (1.87 g, 41%) was obtained.

$^1$H-NMR (CDCl$_3$) δ: 0.55–0.91 (m, 4H), 2.01 and 2.04 (s, 3H, rotamers), 3.19–3.30 (m, 1H), 3.59–3.85 (m, 4H), 5.08 and 5.10 (s, 2H, rotamers), 7.31–7.40 (m, 5H).

FAB MS (m/z); 289 (M$^+$+H), 245, 199, 152, 135, 91

EXAMPLE 28

7-(S)-[Benzyloxycarbonylamino]-5-[2.4]heptane

In ethanol (5.0 ml) was dissolved 7-(S)-[benzyloxycarbonylamino]-5-N-acetylazaspiro[2.4]heptane (288 mg, 1.0 mmol). At room temperature, a 5 mol/l aqueous solution (10 ml) of sodium hydroxide was added. The mixture was stirred at room temperature for 72 hours. The reaction mixture was separated by the addition of toluene and water. The organic layer was washed with water. The organic layer was dried over sodium sulfate, filtered, and then evaporated under reduced pressure to give a yellow oil (165 mg). The resulting oil was purified by a silica gel column, whereby the title compound (97.4 mg, 40%) was obtained.

$^1$H-NMR (CDCl$_3$) δ: 0.50–0.82 (m, 4H), 2.74 (d, J=10.7 Hz, 1H), 2.94–3.02 (m, 2H), 3.34 (dd, J=5.5 and 11.5 Hz, 1H), 3.71 (m, 1H), 5.07 (s, 2H), 7.28–7.39 (m, 5H).

FAB MS (m/z); 247 (M$^+$+H), 185, 157, 135, 91

EXAMPLE 29

7-(S)-[Benzyloxycarbonylamino]-5-[2.4]heptane p-toluenesulfonate

In toluene (1.2 ml) was dissolved 7-(S)-[benzyloxycarbonylamino]-5-azaspiro[2.4]heptane (123 mg, 0.5 mmol). At room temperature, an ethanol solution of p-toluenesulfonate monohydrate (95.1 mg, 0.5 mmol) was added. The resulting mixture was stirred at room temperature for 1 hour. The reaction mixture was concentrated under reduced pressure. Ethyl acetate (2.0 ml) was added to the residue and the mixture was subjected to slurry stirring at 50° C. for 30 minutes. Diisopropyl ether (2.0 ml) was added, followed by slurry stirring at room temperature for 30 minutes. The crystals thus precipitated were collected by filtration and then washed with a mixture (1:1) of ethyl acetate and diisopropyl ether. The crystals were dried under reduced pressure at room temperature, whereby the title compound (150 mg, 71%) was obtained as white crystals.

$^1$H-NMR (CDCl$_3$) δ: 0.55–0.98 (m, 4H), 2.32 (s, 3H), 3.04–3.12 (m, 1H), 3.54–3.64 (m, 3H), 3.91 (m, 1H), 5.02 (dd, J=12.5 and 15.5 Hz, 2H), 6.59 (d, J=7.6 Hz, 1H), 7.06 (d, J=7.9 Hz, 2H), 7.27–7.34 (m, 5H), 7.70 (d, J=7.9 Hz, 2H), 9.06 (br.s, 1H), 9.35 (br.s, 1H).

INDUSTRIAL APPLICABILITY

The invention according to the present application makes it possible to prepare, in an easy and convenient manner, an amino-substituted azaspiroalkane compound having a spirocyclic structure, which compound is an intermediate compound serving as a raw material for the synthesis of a synthetic antibacterial compound.

What is claimed is:

1. A compound represented by the formula (I):

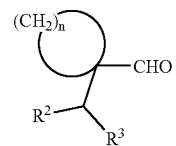

(I)

wherein, n stands for an integer of from 2 to 5; and R$^2$ and R$^3$ each independently represents a C$_{1-4}$ alkoxy group.

2. The compound of claim 1, wherein R$^2$ and R$^3$ each represents an ethoxy group.

3. A compound of represented by the formula (I):

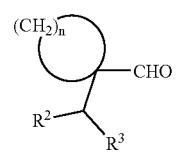

(I)

wherein n stands for an integer of 2; and R$^2$ and R$^3$ each independently represents a C$_{1-4}$ alkoxy group or may be integrated together to form a group represented by the formula:

—O—(CH$_2$)$_m$—O— wherein, m stands for an integer of from 1 to 4.

* * * * *

UNITED STATES PATENT AND TRADEMARK OFFICE
CERTIFICATE OF CORRECTION

PATENT NO. : 7,074,837 B2
APPLICATION NO. : 10/344272
DATED : July 11, 2006
INVENTOR(S) : Keiji Nakayama et al.

It is certified that error appears in the above-identified patent and that said Letters Patent is hereby corrected as shown below:

Title page
Under (30) Foreign Application Priority Data:

Feb. 21, 2001      (JP)      ...................................................2001-044402

Insert:
    Aug. 8, 2000      (JP)      ...................................................2000-239246
    Feb. 5, 2001      (JP)      ...................................................2001-027632
    Feb. 13, 2001      (JP)      ...................................................2001-034779
    Jun. 8, 2001      (JP)      ...................................................2001-173426

Signed and Sealed this

Twenty-first Day of August, 2007

JON W. DUDAS
*Director of the United States Patent and Trademark Office*